United States Patent
Van Rijswijck et al.

(10) Patent No.: US 6,710,223 B1
(45) Date of Patent: *Mar. 23, 2004

(54) METHOD FOR IMPROVING SKIN CONDITION

(75) Inventors: Laura Graves Spalding Van Rijswijck, Burlington, KY (US); Gretchen Louise Elder, Blue Ash, OH (US); Mauricio Rolando Odio, Gahanna, OH (US); Susan Baldwin, Cincinnati, OH (US); Michelle Denise Roseman, Cincinatti, OH (US); Kevin Eugene Grandison, Miami, FL (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 436 days.

(21) Appl. No.: 08/926,533

(22) Filed: Sep. 10, 1997

(51) Int. Cl.[7] ................................................ A61F 13/15
(52) U.S. Cl. ........................ 604/367; 604/359; 604/360
(58) Field of Search ................................. 604/358, 367, 604/359, 360; 424/76.1–76.4, 404, 402; 428/143, 144, 357, 361; 442/123, 152, 153, 154, 170

(56) References Cited

U.S. PATENT DOCUMENTS

| | | |
|---|---|---|
| 2,804,424 A | 8/1957 | Stirn et al. |
| 3,490,454 A | 1/1970 | Goldfarb et al. |
| 3,902,493 A | 9/1975 | Baier et al. |
| 4,112,167 A | 9/1978 | Dake et al. |
| 4,324,247 A | 4/1982 | Aziz |
| 4,513,051 A | 4/1985 | Lavash |
| 4,556,560 A | 12/1985 | Buckingham |
| 4,704,112 A | 11/1987 | Suzuki et al. |
| 4,882,204 A | 11/1989 | Tenenbaum |
| 4,900,317 A | 2/1990 | Buell |
| 4,904,524 A | 2/1990 | Yoh |
| 4,990,144 A | 2/1991 | Blott |
| 4,996,238 A | 2/1991 | Matravers |
| 5,043,155 A | 8/1991 | Puchalski et al. |
| 5,370,132 A | 12/1994 | Weber et al. |
| 5,509,915 A | 4/1996 | Hanson et al. |
| 5,525,346 A | 6/1996 | Hartung et al. |
| 5,558,655 A | 9/1996 | Jezzi et al. |
| 5,607,760 A * | 3/1997 | Roe ........................ 604/358 |
| 5,609,587 A | 3/1997 | Roe |
| 5,643,588 A | 7/1997 | Roe et al. |

FOREIGN PATENT DOCUMENTS

| | | |
|---|---|---|
| DE | 3309530 C1 | 10/1984 |
| EP | 0 297 828 A1 | 1/1989 |
| EP | 0 631 768 A1 | 1/1995 |
| EP | 0 692 263 B1 | 1/1996 |
| GB | 2033751 A | 5/1980 |

* cited by examiner

*Primary Examiner*—Weilun Lo
*Assistant Examiner*—Jacqueline F Stephens
(74) *Attorney, Agent, or Firm*—Edward J. Milbrada; Ken K. Patel; Steven W. Miller

(57) ABSTRACT

The present invention relates a method for improving skin condition by repeatedly applying lotion-treated absorbent articles to a wearer. When applied with sufficient frequency, the skin in the area covered by lotion-treated absorbent articles shows improvement in skin smoothness, relative to skin covered by untreated absorbent articles that do not comprise a skin care composition. The present invention also relates to methods for assessing skin smoothness in the area covered by an absorbent article.

37 Claims, 3 Drawing Sheets

METHOD FOR IMPROVING SKIN CONDITION

TECHNICAL FIELD

This application relates to a method for improving skin condition in wearers of absorbent articles such as diapers, training pants, adult incontinence devices, feminine hygiene products, and the like. More particularly, the application relates to a method comprising the repeated use of absorbent articles that deliver a composition to the wearer's skin, so as to improve skin smoothness.

BACKGROUND OF THE INVENTION

Many types of disposable absorbent products, such as diapers, are available that have a high capacity for absorbing urine and other body exudates. Disposable products of this type generally comprise some sort of liquid-pervious topsheet material, an absorbent core, and a liquid-impervious backsheet material. Although these types of absorbent structures may be highly efficient for the absorption of liquids, it is well recognized that long-term wear of such structures may lead to skin which is compromised in terms of being over hydrated or exposed to skin irritants commonly found in body exudates. It is generally known that skin under absorbent articles is more susceptible to skin disorders, including diaper rash, erythema (i.e., redness), heat rash, abrasion, pressure marks and skin barrier loss. Most of the cutaneous symptomatology associated with the above conditions is readily apparent upon visual inspection of the skin. However, it also well recognized that the hydration effects associated with routine use of absorbent articles can elicit alterations in the structure and function of the skin that, while not apparent to the naked eye (i.e., subclinical effects), may predispose the epidermis to subsequent damage and/or may alter it in ways that render it less aesthetically pleasing to other senses such as touch. Indeed, alterations in the microtopography of the skin are often detectable to the touch and generally perceived as an increase in the roughness of the skin (i.e., less smooth skin).

To address the concerns of skin disorders or alterations associated with wearing absorbent articles, the caregiver often applies skin conditioning or protective products such as Vaseline®, baby lotions, ointments, powders, etc. to the buttocks, genitals, anal and/or other regions before placing the absorbent article on the wearer. This procedure usually involves the caregiver applying the skin protective product to their hands, and then wiping the same on the skin of the infant. To eliminate the need for this wasteful, messy, time-consuming, and easily forgotten procedure, there have been attempts to prepare absorbent articles which contain a protective or therapeutic skin care substance on the article's topsheet.

U.S. Pat. No. 3,585,998 to Hayford et al. teaches a disposable baby diaper, an interior liner of which carries an array of pressure-rupturable capsules containing baby oil. The patent teaches that it is desirable to break the capsules prior to using the diaper by applying pressure with such household items as a rolling pin, hand iron, etc. Articles disclosed by this patent have serious drawbacks. Namely, unless the capsules are ruptured by applying pressure prior to using the diaper or the bandage, the skin-care substance contained in the capsules is either not delivered at all or is delivered non-uniformly leaving some areas of skin uncoated.

U.S. Pat. No. 3,489,148 to Duncan et al. teaches a baby diaper comprising a hydrophobic and oleophobic topsheet wherein a portion of the topsheet is coated with a discontinuous film of oleaginous material. A major disadvantage of the diapers disclosed in the Duncan et al. reference is that the hydrophobic and oleophobic topsheets are slow in promoting transfer of urine to the underlying absorbent cores.

U.S. Pat. No. 5,643,588 to Roe et al. addresses some of the concerns presented by prior absorbent articles which were designed to deliver a skin protective material. In particular, Roe describes an absorbent article whose topsheet is surface treated with a lotion that comprises an emollient for facilitating easier cleaning of feces and other exudates and an agent which immobilizes the lotion so that it does not migrate from the point of initial application.

While the prior art describes articles designed to deliver compositions to provide skin care benefits, the prior art has failed to describe a regimen which results in improved skin condition in regions of the wearer's body covered by absorbent articles, where the regimen does not require intervention from the caregiver in the form of manual application of skin care compositions. That is, the prior art has not recognized the importance of the repeated use of absorbent articles that automatically deliver sufficient levels of a composition to the wearer's skin that allows the improvement of skin condition in the region of the wearer covered by absorbent articles.

Accordingly, it would be desirable to provide a method: (1) wherein the condition of skin covered by the absorbent article is improved; and (2) that does not require intervention by the wearer or caregiver in the form of manual application of skin care agents.

Therefore, it is an object of the present invention to provide a method for improving skin condition of an absorbent article wearer comprising repeated application of disposable absorbent articles that automatically deliver sufficient levels of a composition. In this regard, it is an object of the present invention to provide a method that comprises application of absorbent articles which have a composition on a wearer-contacting surface, where the composition is transferable to the wearer's skin and is effective at improving skin condition.

These and other objects are obtained in accordance with the present invention, as will become readily apparent upon reading the following disclosure.

SUMMARY OF THE INVENTION

The present invention relates to a method for improving skin condition of a wearer in the area covered by an absorbent article, the method comprising the following steps:
(a) applying to the wearer an absorbent article having a skin care composition that improves skin smoothness upon transfer to the skin of the wearer;
(b) transferring to the wearer at least a portion of the skin care composition during wear; and
(c) repeating steps (a) and (b) with one or more additional articles with sufficient frequency to improve skin smoothness in the area covered by the absorbent article relative to skin covered by an equivalent absorbent article that does not comprise the skin care composition, and without the need for manual application of skin protective agents or condition agents (e.g., by the caregiver or wearer).

DETAILED DESCRIPTION OF THE INVENTION

I. Definitions

Figure 1:
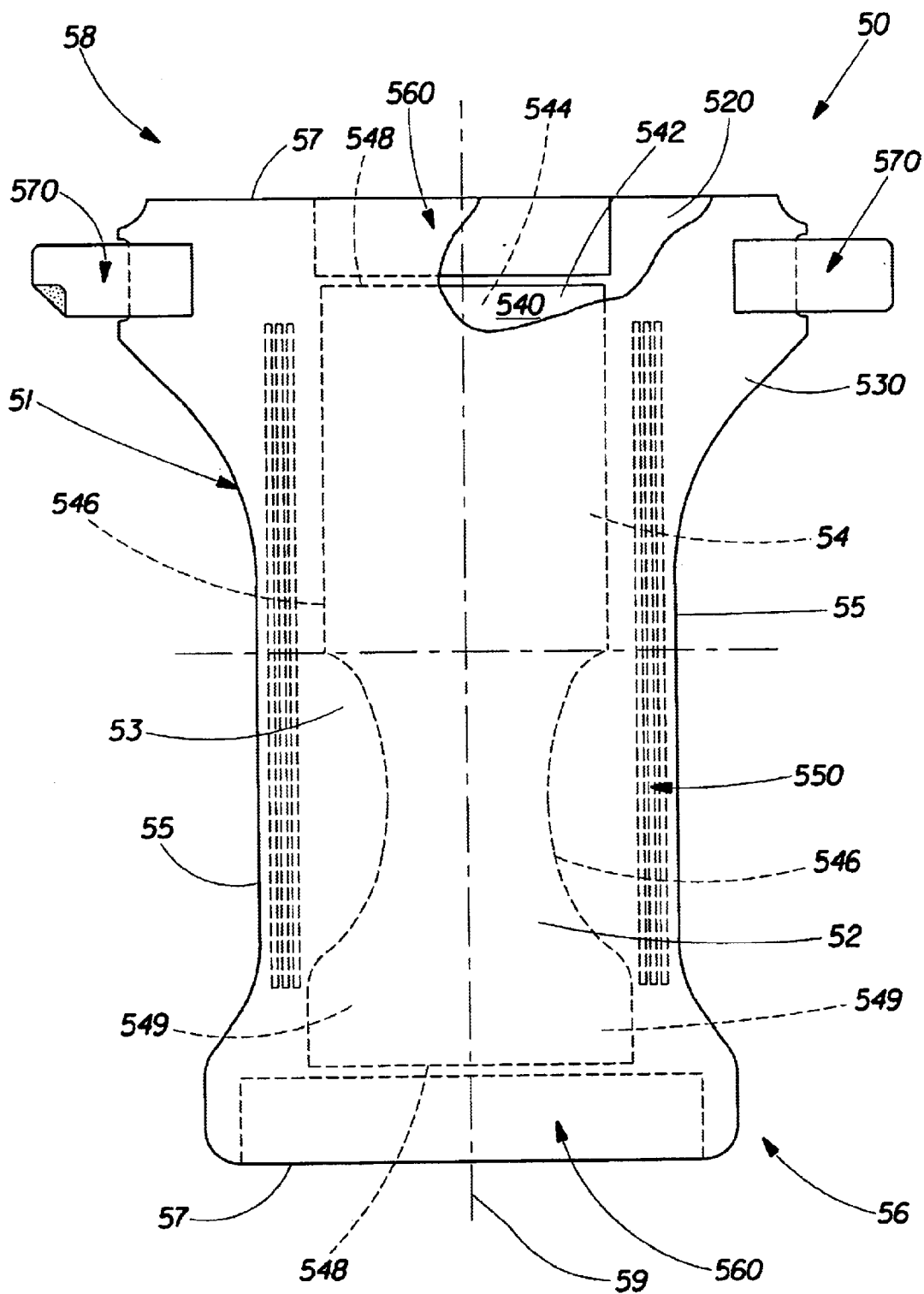
FIG. 1 is an absorbent article in the form of a diaper according to the present invention.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the term "skin care composition" refers to any composition which comprises one or more agents which, when transferred from an article to a wearer's skin, improves the smoothness of the skin. Representative materials are discussed in detail below.

As used herein, the term "skin smoothness" is used to refer to tactile skin properties that encompass one or more of the following: roughness, suppleness, elasticity, softness, friction, dryness, scaling, and pliability.

As used herein, the term "treated article" means an absorbent article having a skin care composition on or migratable to at least one wearer-contacting surface of that article. An "untreated aricle that does not comprise a skin care composition" is an article that is substantially the same as a treated article, in terms of topsheet, backsheet, absorbent core, chassis design, cuffs, etc., but which does not comprise a skin care composition that is transferred to the wearer during use.

As used herein, the term "wearer-contacting surface" of an absorbent article is one or more surfaces of any article components that contact the wearer at some time during the wear period. Wearer contacting surfaces include, but are not limited to, portions of the topsheet, leg cuffs, waist region, side panels, fastening tabs, etc., which contact a wearer during use.

Other terms are defined in the specification where initially discussed.

With respect to the skin care composition, all percentages, ratios and proportions used herein are by weight unless otherwise specified.

II. Method for Improving Skin Condition

As discussed, the adverse skin effects that result from the occlusive nature of current absorbent articles are well recognized. Efforts have been made to overcome these negative attributes by preparing articles that deliver beneficial compositions. However, Applicants are the first to recognize the benefit of a method comprising frequent cycles of cumulative delivery of a skin care composition to the wearer's skin to improve skin condition. In this regard, the present invention relates to a method for improving skin condition of a wearer in the area covered by an absorbent article, the method comprising the following steps:

(a) applying to the wearer an absorbent article having a skin care composition that improves skin smoothness upon transfer to the skin of the wearer;

(b) transferring to the wearer at least a portion of the skin care composition during wear; and (c) repeating steps (a) and (b) with one or more additional articles with sufficient frequency to improve skin smoothness in the area covered by the absorbent article relative to skin covered by an equivalent absorbent article that does not comprise the skin care composition, and without the need for manual application of skin protective agents or condition agents (e.g., by the caregiver or wearer).

Applicants have discovered that, surprisingly, improving smoothness of skin covered by absorbent articles can be accomplished coincidentally (or "automatically") with repeated use, over a period of time (e.g., several days), of absorbent articles that are treated with a composition that is transferred to the wearer under normal usage conditions (e.g., contact, movement, handling by the caregiver after application of the article, body heat, etc.). Thus, while prior attempts to address skin conditions associated with wearing absorbent articles have generally described transfer of a protective material per step (b) above, those prior attempts did not recognize the importance of enhancing skin smoothness per step (a). More importantly, none of those attempts appreciated the importance of step (c), corresponding to frequent cycles of cumulative delivery of a skin care composition to the wearer's skin to improve skin condition. Applicants have further discovered that delivery of relatively low levels of the composition with each article wear are sufficient to obtain the skin benefits resulting from this novel method of cumulative composition delivery.

The treated article used in the present methods provides an available source from which the skin care composition transfers onto the skin continuously over time. As the composition is transferred, it accumulates on the skin surface to improve the skin's smoothness. As a used article is discarded and replaced by a new one, this cycle is repeated for further composition accumulation above and beyond what a single or original article would have delivered on its own. Certain of the ingredients for use in the composition are known to penetrate the stratum corneum (e.g., petrolatum, which is preferred for use herein). Thus, even as some amount of the composition is removed by cleaning, bathing, etc., or even if usage of treated articles as described herein is discontinued temporarily, some of the benefits of the skin composition will remain with the user. As usage of treated articles is resumed before all of the benefits of the composition have dissipated, the user will derive benefits, in terms of skin smoothness, more rapidly than would a user who has not used treated articles.

As indicated above, it is generally recognized that skin under absorbent articles is more susceptible to degradation of that skin's condition. Typically, cutaneous manifestations of these skin conditions include redness (also referred to as erythema) and/or rash. Sub-clinical changes to the skin which, although not visible to the naked eye, also take place as a result of wearing an absorbent article. These changes are usually perceivable by touch and/or visually as changes to the surface texture of the skin. The perception of skin textural features is influenced by physiological properties of the skin such as elasticity (mainly a factor of the dermis) and pliability (primarily a stratum corneum property). Thus, in addition to direct evaluation of skin smoothness (i.e., skin topography), assessment of related skin characteristics such as friction, elasticity, suppleness, and the like, are relevant to the overall assessment of skin smoothness.

As such, Applicants describe herein a method for improving skin condition in regions covered by an absorbent article, wherein the desired endpoint of the method is the improvement of skin smoothness as measured using skin cast replicas (roughness) and D-Squame tape samples (scaling). In brief, the protocols for measuring skin smoothness determine whether use of a test article results in improvements in skin smoothness in the skin regions compared to use of an equivalent, untreated article. The test method involves comparison between 2 groups of subjects who are assigned to wear the test or the control product for 1 week (a baseline week in which all subjects use the same control product is included prior to initiating the 1-week product comparison portion of the study). Per this approach, the skin smoothness in the region covered by the absorbent article of the users of the articles is determined by well accepted skin casting and corneocyte shedding (D-Squame tape) methods at the beginning and at the end of the treatment phase of the study (product comparison week). Detailed protocols for assessing skin smoothness via skin cast replicas and D-Squame tape analysis are described in detail in the Test Method section below.

In one aspect, the improvement manifests itself as a statistically significant difference in skin cast replicas or D-Squame tape analysis at a 90% confidence level, relative to skin covered by an equivalent absorbent article that does not comprise the skin care composition. In this regard, it is preferred that the skin smoothness improvement manifests itself at a 95% confidence level.

Separately, it is recognized that one may observe large between-group differences (i.e., in the mean) in skin smoothness scores, yet due to large inter-subject variability fail to observe traditional statistically significant differences. In this regard, improvements of at least about 10% between group (control and test) means, though not necessarily statistical, may be recognized and appreciated by caregivers and users as providing skin smoothness benefits. In this regard, the methods of the present invention will result in improvements in smoothness scores of at least about 10%, more preferably at least about 15%, still more preferably at least about 20%.

For purposes of the present disclosure, evidence of a test product improvement is demonstrated with skin cast and/or D-Squame and is defined as a statistical or non-statistical difference: (a) for the study group as a whole; or (b) for any gender or age or diaper size subset of the study group; or (c) any Visit 2 grade subset for the D-Squame test.

III. Skin Care Composition

While the specific composition(s) delivered (referred to herein as "skin care composition" and "composition") in accordance with the present method is not the critical factor in achieving improved skin condition of the area under the absorbent article, it is apparent that the composition must provide either a protective, nonocclusive function (e.g., a relatively liquid impervious but vapor pervious barrier) to avoid skin hyperhydration and skin exposure to materials contained in body exudates, or it must contain agents that deliver, either directly or indirectly, skin care benefits. For example, indirect benefits include improved removal of skin irritants such as feces or urine. The composition may be in a variety of forms, including, but not limited to, emulsions, lotions, creams, ointments, salves, powders, suspensions, encapsulations, gels, and the like.

As used herein, the term "effective amount of a skin care composition" refers to an amount of a particular composition which, when applied or migrated to one or more of the wearer-contacting surface(s) of an absorbent article(s), will be effective in providing a protective barrier and/or delivering a skin care benefit when delivered via absorbent articles over time. Of course, the effective amount of composition applied to the article will depend, to a large extent, on the particular composition used. Nonetheless, the quantity of the composition on at least a portion of the wearer-contacting surface of the absorbent article will preferably range from about 0.05 mg/in$^2$ (0.0078 mg/cm$^2$) to about 80 mg/in$^2$ (12.4 mg/cm$^2$), more preferably from about 1 mg/in$^2$ (0.16 mg/cm$^2$) to about 40 mg/in$^2$ (6.20 mg/cm$^2$), still more preferably from about 4 mg/in$^2$ (0.62 mg/cm$^2$) to about 26 mg/in$^2$ (4.03mg/cm$^2$). These ranges are by way of illustration only and the skilled artisan will recognize that the nature of the composition will dictate the level that must be applied to achieve the desired skin benefits, and that such levels are ascertainable by routine experimentation in light of the present disclosure.

While the level of skin care composition applied to the absorbent article is an important aspect of the present methods, more important is the amount of composition transferred to the wearer's skin during use of one or more treated articles. Though the requisite level delivered to the skin to provide the desired skin benefits will depend to some degree on the nature of the composition employed, Applicants have found that relatively low levels may be delivered while still providing the desired skin effects. This is particularly true for preferred compositions, such as that described in Example 1.

Another benefit of the present method is the controlled application of the skin care composition to deliver the low but effective levels of composition required. This is in contrast to typically sporadic manual application of skin care agents, where the caregiver/user often applies significantly greater levels of material than are needed. Excessive materials added manually may adversely impact the fluid handling properties of the absorbent article, as a result of transfer from the skin to the article. Indeed, for certain materials, such as petrolatum, the levels applied manually may actually result in an occlusive effect, thereby compromising the skin. A benefit of the present methods is providing a barrier to surface moisture while avoiding occlusion of the skin (i.e., maintaining skin breathability). Thus, the present methods, which allow controlled composition delivery throughout the wear period, allow transfer of optimal levels of the composition to the skin to improve skin condition.

The method for determining the amount of skin care composition transferred to a wearer's skin after wearing one or more treated articles is described in the Test Methods section below. With regard to the level of skin care composition that is transferred to the wearer during use of one treated absorbent article worn for a period of about 3 hours (a typical daytime wear time), particularly for preferred skin care compositions such as that described in Example 1, preferred is where at least about 0.01 mg/in$^2$ (0.0016 mg/cm$^2$), more preferably at least about 0.05 mg/in$^2$ (0.0078 mg/cm$^2$), still more preferably at least about 0.1 mg/in$^2$ (0.016 mg/cm$^2$), of the composition is transferred to the skin over a three hour wear period. Typically, the amount of composition delivered by one treated article will be from about 0.01 mg/in$^2$ (0.0016 mg/cm$^2$) to about 5 mg/in$^2$ (0.78 mg/cm$^2$), more preferably from about 0.05 mg/in$^2$ (0.0078 mg/cm$^2$) to about 3 mg/in$^2$ (0.47 mg/cm$^2$), still more preferably from about 0.1 mg/in$^2$ (0.016 mg/cm$^2$) to about 2 mg/in$^2$ (0.31 mg/cm$^2$), over a three hour wear period.

For continual use of treated articles (in other words, changes occur in accordance with normal use patterns, which typically include changes every 3 to 4 hours during the day and a fresh article before overnight sleep) such as for a period of 24 hours, it will be preferred that at least about 0.03 mg/in$^2$ (0.0047 mg/cm$^2$), more preferably at least about 0.1 mg/in$^2$ (0.016 mg/cm$^2$), still more preferably at least about 0.3 mg/in$^2$ (0.047 mg/cm$^2$), of the composition is transferred to the wearer's skin over the 24 hour period.

Typically, the amount of composition delivered after a period of 24 hours where treated articles are applied at each change, will be from about 0.03 mg/in$^2$ (0.0047 mg/cm$^2$) to about 18 mg/in$^2$ (2.79 mg/cm$^2$), more typically from about 0.1 mg/in$^2$ (0.016 mg/cm$^2$) to about 10 mg/in$^2$ (1.55 mg/cm$^2$), still more typically from about 0.3 mg/in$^2$ (0.047 mg/cm$^2$) to about 6 mg/in$^2$ (0.93 mg/cm$^2$).

It will be recognized that of the numerous materials useful in the skin care compositions delivered to skin in accordance with the present methods, those that have been deemed safe and effective skin care agents are logical materials for use herein. Such materials include Category I actives as defined by the U.S. Federal Food and Drug Administration's (FDA) Tentative Final Monograph on Skin Protectant Drug Products for Over-the-Counter Human Use, which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use tentative final monograph on skin protectant drug products for over-the-counter human use, which presently include: live yeast cell derivatives, aldioxa, aluminum acetate, microporous cellulose, cholecalciferol, colloidal oatmeal, cysteine hydrochloride, dexpanthanol, Peruvian balsam oil, protein hydrolysates, racemethionine, sodium bicarbonate, Vitamin A, and the like.

Many of the FDA monographed skin care ingredients are currently utilized in commercially available skin care products, such as A and D® Ointment, Vaseline® Petroleum Jelly, Desitin® Diaper Rash Ointment and Daily Care Ointment, Gold Bond® Medicated Baby Powder, Aquaphor® Healing Ointment, Baby Magic® Baby Lotion, Johnson's Ultra Sensitive® Baby Cream, Johnson's baby lotion, lip balms, etc. These commercial products may be applied to absorbent articles to create treated articles for use in the present methods, either with or without modification of the product to facilitate delivery via this novel method.

As will be discussed hereinafter, the skin care compositions useful in the methods of the present invention preferably, though not necessarily, have a melting profile such that they are relatively immobile and localized on the wearer-contacting surface of the article at room temperature, are readily transferable to the wearer at body temperature, and yet are not completely liquid under extreme storage conditions. Preferably, the compositions are easily transferable to the skin by way of normal contact, wearer motion, and/or body heat. Because the composition preferably is substantially immobilized on the article's wearer-contacting surface, relatively low levels of composition are needed to impart the desired skin care benefits. In addition, special barrier or wrapping materials may be unnecessary in packaging the treated articles useful in the methods of the present invention.

In a preferred embodiment, the skin care compositions useful herein are solid, or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes some minor liquid components. Preferably, the compositions of the present invention have a zero shear viscosity between about 1.0×10$^6$ centipoise and about 1.0× 10$^8$. More preferably, the zero shear viscosity is between about 5.0×10$^6$ centipoise and about 5.0×10$^7$ centipoise. As used herein the term "zero shear viscosity" refers to a viscosity measured at very low shear rates (e.g., 1.0 sec$^{-1}$) using plate and cone viscometer (a suitable instrument is available fom TA Instruments of New Castle, Del. as model number CSL 100). One of skill in the art will recognize means other than high melting point components (as discussed below) can be used to provide comparable viscosities measured for such compositions comprising such means can be measured by extrapolating a plot of viscosity vs. shear rate for such compositions to a shear rate of zero at a temperature of about 20° C.

Preferred compositions are at least semi-solid at room temperature to minimize composition migration. In addition, the compositions preferably have a final melting point (100% liquid) above potential "stressful" storage conditions that can be greater than 45° C. (e.g., warehouse in Arizona, car trunk in Florida, etc.). Representative compositions having these melt characteristics are described in detail in U.S. Pat. No. 5,643,588 (Roe et al.), U.S. Pat. No. 5,607,760 (Roe et al.), U.S. Pat. No. 5,609,587, and U.S. Pat. No. 5,635,191, the disclosure of each of which is incorporated herein by reference. Specifically, preferred compositions will have the following melt profile:

| Characteristic | Preferred Range | Most Preferred |
| --- | --- | --- |
| % liquid at room temp. (20° C.) | 2–50 | 3–25 |
| % liquid at body temp. (37° C.) | 25–95 | 30–90 |
| final melting point (° C.) | ≧38 | ≧45 |

By being solid or semisolid at ambient temperatures, preferred compositions do not have a tendency to flow and migrate to a significant degree to undesired locations of the article to which they are applied. This means less skin care composition is required for imparting desirable therapeutic, protective or conditioning benefits.

To enhance immobility of preferred compositions, the viscosity of the formulated compositions should be as high as possible to prevent flow within the article to undesired location. Unfortunately, in some instances, higher viscosities may inhibit transfer of composition to the wearer's skin. Therefore, a balance should be achieved so the viscosities are high enough to keep the compositions localized on the surface of the article, but not so high as to impede transfer to the wearer's skin. Suitable viscosities for the compositions will typically range from about 5 to about 500 centipoise, preferably from about 5 to about 300 centipoise, more preferably from about 5 to about 100 centipoise, measured at 60° C. using a rotational viscometer (a suitable viscometer is available from Lab Line Instruments, Inc. of Melrose Park, Ill. as Model 4537). The viscometer is operated at 60 rpm using a number 2 spindle.

For compositions designed to provide a skin smoothness benefit, a useful active ingredient in these compositions is one or more skin protectants or emollients. As used herein, the term "emollient" is a material that protects against wetness or irritation, softens, soothes, supples, coats, lubricates, moisturizes, protects and/or cleanses the skin. (It will be recognized that several of the monographed actives listed above are "emollients", as that term is used herein.) In a preferred embodiment, these emollients will have either a plastic or liquid consistency at ambient temperatures, i.e., 20° C. This particular emollient consistency allows the composition to impart a soft, lubricious, lotion-like feel.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_{12}$–$C_{28}$ fatty acids; triethylene glycol and derivatives thereof; spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids e.g., lactic acid, such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

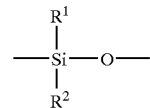

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the article by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Suitable humectants include glycerine, propylene glycol, sorbitol, trihydroxy stearin, and the like.

When present, the amount of emollient that can be included in the composition will depend on a variety of factors, including the particular emollient involved, the lotion-like benefits desired, the other components in the composition and like factors. The composition will comprise from 0 to about 100%, by total weight, of the emollient. Preferably, the composition will comprise from about 10 to about 95%, more preferably from about 20 to about 80%, and most preferably from about 40 to about 75%, by weight, of the emollient.

Another optional, preferred component of the therapeutic/skin protective/skin conditioning compositions useful in the methods of the present invention is an agent capable of immobilizing the composition (including the preferred emollient and/or other skin conditioning/therapeutic/protective agents) in the desired location in or on the treated article. Because certain of the preferred emollients in the composition have a plastic or liquid consistency at 20° C., they tend to flow or migrate, even when subjected to modest shear. When applied to a wearer-contacting surface or other location of an absorbent article, especially in a melted or molten state, the emollient will not remain primarily in or on the treated region. Instead, the emollient will tend to migrate and flow to undesired regions of the article.

Specifically, if the emollient migrates into the interior of the article, it can cause undesired effects on the absorbency of the article core due to the hydrophobic characteristics of many of the emollients and other skin conditioning agents used in the compositions useful in the methods of the present invention. It also means that much more emollient has to be applied to the article to get the desired skin smoothness benefits. Increasing the level of emollient not only increases the cost, but also exacerbates the undesirable effect on the absorbency of the article's core and undesired transfer of composition during processing/converting of the treated articles.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the article's wearer contacting surface or in the region to which it is applied.

It is also advantageous to "lock" the immobilizing agent on the wearer contacting surface or the region of the article to which it is applied. This can be accomplished by using immobilizing agents which quickly set up (i.e., solidify) upon application to the article. In addition, outside cooling of the treated article via blowers, fans, cold rolls, etc. can speed up crystallization of the immobilizing agent.

In addition to being miscible with (or solubilized in) the emollient, the immobilizing agent will preferably have a melting profile that will provide a composition that is solid or semisolid at ambient temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

When utilized, immobilizing agents useful herein can be selected from any of a number of agents, so long as the preferred properties of the skin care composition provide the skin benefits described herein. Preferred immobilizing agents will comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably crystalline high melting materials selected from the group consisting of cetyl alcohol, stearyl alcohol, behenyl alcohol, and mixtures thereof. (The linear structure of these materials can speed up solidification on the treated absorbent article.) Mixtures of cetyl alcohol and stearyl alcohol are particularly preferred. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{18}$ fatty alcohols increase the rate of crystallization of the composition causing the composition to crystallize rapidly onto the surface of the substrate.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the article. Addionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S.P. 434 from Strahl and Pitsch Inc. P.O. Box 1098 West Babylon, N.Y. 11704.

Suitable polyhydroxy fatty acid esters for use in the present invention will have the formula:

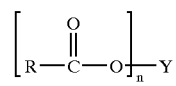

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di-stearate and sucrose mono- and di- laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174, 927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —CH($CH_2OH$)-[($CHOH)_{n-1}$]—$CH_2OH$, —$CH_2OH$—$CH_2$—($CHOH)_2$($CHOR^3$)($CHOH$)—$CH2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

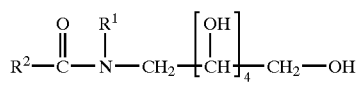

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}$($OCH_2CH_2)_n$OH, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, beeswax, candelilla, paraffin, ceresin, esparto, ouricuri, rezowax, and other known waxes. Preferably the wax is a paraffin wax. An example of a particularly preferred paraffin wax is Parrafin S.P. 434 from Strahl and Pitsch Inc. P.O. Box 1098 West Babylon, N.Y. 11704.

The amount of the optional immobilizing agent that can be included in the composition will depend on a variety of factors, including the actives (e.g., emollients) involved, the particular immobilizing agent involved, the other components in the composition, whether an emulsifier is required to solubilize the immobilizing agent in the other components, and like factors. When present, the composition will typically comprise from about 5 to about 90% of the immobilizing agent. Preferably, the composition will comprise from about 5 to about 50%, most preferably from about 10 to about 40%, of the immobilizing agent.

Of course, it is highly desirable that at least a portion of the article's topsheet be made of a hydrophilic material to promote rapid transfer of liquids (e.g., urine) through the topsheet. Similarly, it may be desirable that the composition be sufficiently wettable to ensure that liquids will transfer through the topsheet rapidly. Alternatively, hydrophobic skin care composition may be utilized, so long as they are applied such that the fluid handling properties of the topsheet are adequately maintained. (For example, as discussed below, nonuniform application of the composition to the topsheet is one means to accomplish this goal.) This diminishes the likelihood that body exudates will flow off the composition-treated topsheet rather than being drawn through the topsheet and being absorbed by the absorbent core.

Where a hydrophilic composition is desired, depending upon the particular components used in the composition, a hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$–$C_{18}$ fatty alcohols having HLB values below about 7 may require addition of hydrophilic surfactant to improve wettability when the composition is applied to article topsheets. Similarly, a hydrophobic emollient such as petrolatum may require the addition of a hydrophilic surfactant if hydrophilic composition is desired. Of course, the concern around wettability is not a factor when the wearer-contacting surface under consideration is other than the article's topsheet or when fluid handling properties of the topsheet are adequately maintained via other means (e.g., nonuniform application).

Suitable hydrophilic surfactants will preferably be miscible with the other components of the skin care composition so as to form blended mixtures. Because of possible skin sensitivity of those using disposable absorbent products to which the composition is applied, these surfactants should also be relatively mild and non-irritating to the skin. Typically, these hydrophilic surfactants are nonionic to be not only non-irritating to the skin, but also to avoid other undesirable effects on any other structures within the treated article. For example, reductions in tissue laminate tensile strength, adhesive bond sufficiencies, and the like.

Suitable nonionic surfactants may be substantially non-migratory after the composition is applied to the article and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in compositions that will be applied to the articles, at least in the liquid discharge region of the diaper, include alkylglycosides; alkylglycoside ethers as described in U.S. Pat. No. 4,011,389 (Langdon, et al), issued Mar. 8, 1977, which is incorporated by reference; alkylpolyethoxylated esters such as Pegosperse 1000MS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25–12 (condensation product of $C_{12}$–$C_{15}$ linear alcohols with 12 moles of ethylene oxide) and NEODOL 23–6.5T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the composition includes Aerosol OT, a dioctyl ester of sodium sulfosuccinic acid marketed by American Cyanamid Company.

Still another type of suitable surfactant for use in the composition includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the composition.

The amount of hydrophilic surfactant required to increase the wettability of the composition to a desired level will depend in-part upon the HLB value and level of immobilizing agent, if any, used, the HLB value of the surfactant used and like factors. The composition can comprise from about 0.1 to about 50% of the hydrophilic surfactant when needed to increase the wettability properties of the composition. Preferably, the composition comprises from about 1 to about 25%, most preferably from about 10 to about 20%, of the hydrophilic surfactant when needed to increase wettability.

Compositions can comprise other components typically present in emulsions, creams, ointment, lotions, powders, suspensions, etc. of this type. These components include water, viscosity modifiers, perfumes, disinfectant antibacterial actives, antiviral agents, vitamins, pharmaceutical actives, film formers, deodorants, opacifiers, astringents, solvents, preservatives, and the like. In addition, stabilizers can be added to enhance the shelf life of the composition such as cellulose derivatives, proteins and lecithin. All of these materials are well known in the art as additives for such formulations and can be employed in appropriate amounts in the compositions for use herein.

If water-based skin care compositions are used, a preservative will be needed. Suitable preservatives include propyl paraben, methyl paraben, benzyl alcohol, benzylkonnium, tribasic calcium phosphate, BHT, or acids such as citric, tartaric, maleic, lactic, malic, benzoic, salicylic, and the like. Suitable viscosity increasing agents include some of the agents described as effective immobilizing agents. Other suitable viscosity increasing agents include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Suitable solvents include propylene glycol, glycerine, cyclomethicone, polyethylene glycols, hexalene glycol, diol and multi-hydroxy based solvents. Suitable vitamins include A, D3, E, B5 and E acetate.

IV. Absorbent Article

As used herein, the term "absorbent article" refers to a device which absorbs and retains body exudates. The term "disposable" is used herein to describe absorbent articles which are not intended to be laundered or otherwise restored or reused as an absorbent article after a single use. Examples of disposable absorbent articles include feminine hygiene garments such as sanitary napkins, panti-liners and tampons, diapers, incontinence briefs, diaper holders, training pants, and the like.

Disposable absorbent articles typically comprise a liquid pervious topsheet, a liquid impervious backsheet and an absorbent core positioned between the topsheet and the backsheet. Disposable absorbent articles and components thereof, including the topsheet, backsheet, absorbent core, and any individual layers of these components, have a body facing surface and a garment facing surface. As used herein, "body facing surface" means that surface of the article or component which is intended to be worn toward or adjacent to the body of the wearer, while the "garment facing surface" is on the opposite side and is intended to be worn toward or placed adjacent to the wearer's clothing or undergarments when the disposable absorbent article is worn.

The following description generally discusses the absorbent core, topsheet, and backsheet materials that are useful in disposable absorbent articles that are used in the methods of the present invention. It is to be understood that this general description applies to these components of the specific absorbent articles shown in FIG. 1 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, spunlace, carded, wet-laid, melt-blown, hydroentangled, hydroformed, hydroapertured, combinations of the above, or the like.

The backsheet is impervious to liquids (e.g., menses and/or urine) and is preferably comprises a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. The size of the backsheet is dictated by the size of the absorbent core and the exact absorbent article design selected.

As discussed above, while it is preferred that the composition which is continually, automatically transferred to the wearer's skin by wearing articles described herein be relatively impervious to liquids such as urine and runny feces, it is also preferred that the composition be relatively vapor pervious to provide a nonocclusive barrier for the skin. In this regard, to further improve skin condition in the wearer's region under the absorbent articles via the presently disclosed methods, absorbent articles useful in those methods may also provide "breathability", to facilitate relatively lower relative humidity in the area between the skin and the absorbent article. Recently, attempts have been disclosed that are directed to improving wearer skin condition by allowing the overhydrated skin to dehydrate to a more acceptable level by allowing either air to reach the skin (thus minimizing potential occlusion effects) and/or providing means for removing water vapor from the surface of the skin. Generally, such mechanisms are referred to as "breathability" or "vapor or moisture permeability". Specific examples include feminine hygiene products, such as catamenial products or so-called pantyliners as described in EP-A-0.104.906; EP-A-0.171.041; EP-A-0.710.471; the disclosure of each of which is incorporated herein by reference. Such products generally have relatively low liquid storage capacity when compared, for example, to baby diapers or adult incontinence products, which have theoretical storage capacities more than ten times the capacity of a feminine hygiene product. The "breathable" articles described in these references may be treated with skin care composition as described herein, and such treated articles may be useful in the methods of the present invention.

Such breathable materials can be various kinds of webs, such as films which are rendered air/vapor pervious by aperturing as described in U.S. Pat. No. 5,628,737, which issued in the name of Dobrin, et al. on May 13, 1997, or by exploiting the "microporosity" property as described in EP-A-0.238.200; EP-A-0.288.021; EP-A-0.352.802; EP-A-0.515.501; U.S. Pat. No. 4.713.068, whereby small voids are created within the film similar to very small cracks. WO 94/23107; WO 94/28224; U. S. Pat. No. 4,758,339 which issued in the name of Yeo, et al. on Jul. 19, 1988; and EP-A-0.315.013 all describe alternative breathable materials which can be fibrous textile or non-woven webs, with air/vapor easily penetrating through the relatively large pores of the structure. Such webs, being either treated or untreated with regard to improving their liquid impermeability properties, such as described in EP-A-0.196.654. In WO 95/16562 a laminate of a non-woven with a breathable film is disclosed. Further disclosures such as in WO 95/16746 relate to other materials allowing water molecules to diffuse through. Also, combinations of various materials comprising various layers of any of the above elements are also well known. Absorbent articles using any of the approaches described in these references (each of which is incorporated herein by reference) in combination with delivering a composition as described herein may be used to carry out the methods of the present invention.

The backsheet and the topsheet are positioned adjacent the garment facing surface and the body facing surface, respectively, of the absorbent core. The absorbent core is preferably joined with the topsheet, the backsheet, or both in any manner as is known by attachment means (not shown in FIG. 1) such as those well known in the art. However, embodiments of the present invention are envisioned wherein portions or the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article in which the wearer contacting surface is treated with a composition are diapers. As used herein, the term "diaper" refers to an absorbent article generally worn by infants, and incontinent persons, that is worn about the lower torso of the wearer. In other words, the term "diaper" includes infant diapers, training pants, adult incontinence devices, etc.

FIG. 1 is a plan view of the diaper 50 useful in the methods of the present invention in its flat-out, uncontracted state (i.e., with elastic induced contraction pulled out) with portions of the structure being cut-away to more clearly show the construction of the diaper 50 and with the portion of the diaper 50 which faces away from the wearer (the outer surface) oriented towards the viewer. As shown in FIG. 1, the diaper 50 preferably comprises a liquid pervious topsheet 520; a liquid impervious backsheet 530 joined with the topsheet 520; an absorbent core 540 positioned between the topsheet 520 and the backsheet 530, the absorbent core 540 having a garment facing surface 542, a body facing surface 544, side edges 546, waist edges 548, and ears 549. The diaper 50 preferably further comprises elasticized leg cuffs 550; an elastic waist feature multiply designated as 560; and a fastening system generally multiply designated as 570.

The diaper 50 is shown in FIG. 1 to have an outer surface 52, an inner surface 54 corresponding to the body facing surface which is opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The body facing surface 54 of the diaper 50 comprises that portion of the diaper 50 which is positioned adjacent to the wearer's body during use. The body facing surface 54 generally is formed by at least a portion of the topsheet 520 and other components that may be joined to the topsheet 520, such as leg cuffs 550, as well as any regions to which the topsheet may not extend but which still contact the wearer, such as the waist feature 560, side panels and the like. The outer surface 52 comprises that portion of the diaper 50 which is positioned away from the wearer's body (i.e., the outer surface 52 generally is formed by at least a portion of the backsheet 530 and other components that may be joined to the backsheet 530). The first waist region 56 and the second waist region 58 extend, respectively, from the end edges 57 of the periphery 51 to the lateral centerline 53 of the diaper 50. FIG. 1 also shows the longitudinal centerline 59.

FIG. 1 shows a preferred embodiment of the diaper 50 in which the topsheet 520 and the backsheet 530 have length and width dimensions generally larger than those of the absorbent core 540. The elasticized leg cuffs 550 and the backsheet 530 extend beyond the edges of the absorbent core 540 to thereby form the periphery 51 of the diaper 50.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993. Each of these patents is incorporated herein by reference. Another diaper configuration to which the present invention can be readily adapted are described in U.S. patent application Ser. No. 08/203,456; filed on Feb. 28, 1994 now U.S. Pat. No. 5,554,145 and incorporated herein by reference. The absorbent cores of diapers described in these patents can be adapted in light of the teachings herein to include the absorbent composite of the present invention as an absorbent gelling material described therein.

A topsheet 520 which is particularly suitable for use in the diaper 50, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophilic material to promote rapid transfer of liquids (e.g., urine) through the topsheet. If the topsheet is made of a hydrophobic material, at least portions of the upper surface of the topsheet are treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

Alternatively, the topsheet may be in the form of an apertured formed film, which is preferred in feminine hygiene absorbent articles. Apertured formed films are useful because they are pervious to body liquids and yet non-absorbent and have a reduced tendency to allow liquids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for use in feminine hygiene products is the formed film described in one or more of the above patents and marketed on sanitary napkins by The Procter & Gamble Company of Cincinnati, Ohio as "DRI-WEAVE®."

The body facing surface of the formed film topsheet can be hydrophilic so as to help body liquids to transfer through the topsheet faster than if the body surface was not hydrophilic so as to diminish the likelihood that liquid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., now abandoned which is incorporated by reference. Alternatively, the body facing surface of the topsheet can be made hydrophilic by treating it with a surfactant such as is described in the above referenced U.S. Pat. No. 4,950,254, incorporated herein by reference.

In a preferred embodiment of a diaper as described herein, the backsheet 530 has a modified hourglass shape extending beyond the absorbent core a minimum distance of about 1.3 cm to about 6.4 cm (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent materials for use as the absorbent core of articles useful in the present methods are described, e.g., in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual- Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized waist bands (not shown) and/or elasticized side panels (also not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989, each being incorporated herein by reference. Absorbent articles having elasticized cuffs that are treated with a composition that may be useful herein are disclosed in co-pending U.S. patent application Ser. No. 08/766,386 (P&G Case 6411) and co-pending U.S. patent application Ser. No. 08/840,039 (P&G Case 6590), both of which are incorporated herein by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 570 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. B1 4,662,875, issued to Hirotsu et al. on May 5, 1987; and U.S. Pat. No. 5,151,092, issued to Buell et al. on Sep. 29, 1992; each of which is incorporated herein by reference.

The diaper 50 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

Of course, it will be recognized that any absorbent article design may be utilized to carry out the methods of the present invention, so long as skin care composition is applied to the article so as to be transferred to the skin during use. The disclosure above is merely for illustrative purposes.

The methods of the present invention may also employ training pants to effect delivery of the desired skin care composition. The term "training pants", as used herein, refers to disposable garments having fixed sides and leg openings designed for infant or adults wearers. Training pants (also referred in the art as "pull on" products) are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993, U.S. Pat. No. 5,569,234, issued to Buell et al. on Oct. 29, 1996, U.S. Pat. No. 4,940,464, issued to Van Gompel et al. on Jul. 10, 1990 and U.S. Pat. No. 5,092,861, issued to Nomura et al. on Mar. 3, 1992, the disclosure of each of which is incorporated herein by reference.

Another disposable absorbent article for use in the present methods are incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. No. 07/637,090 filed by Noel, et al. on Jan. 3, 1991 now abandoned (PCT Publication No. WO 92/11830 published on Jul. 23, 1992). The disclosure of each of these references is incorporated herein.

Another disposable absorbent article for use in the present methods are feminine hygiene articles, such as sanitary napkins. Suitable feminine hygiene articles are disclosed in U.S. Pat. No. 4,556,146, issued to Swanson et al. on Dec. 3, 1985, U.S. Pat. No. B14,589,876, issued to Van Tilberg on Apr. 27, 1993, U.S. Pat. No. 4,687,478, issued to Van Tilburg on Aug. 18, 1997, U.S. Pat. No. 4,950,264, issued to Osborn, III on Aug. 21, 1990, U.S. Pat. No. 5,009,653, issued to Osborn, III on Apr. 23, 1991, U.S. Pat. No. 5,267,992, issued to Van Tilburg on Dec. 7, 1993, U.S. Pat. No. 5,389,094, issued to Lavash et al. on Feb. 14, 1995, U.S. Pat. No. 5,413,568, issued to Roach et al. on May 9, 1995, U.S. Pat. No. 5,460,623, issued to Emenaker et al. on Oct. 24, 1995, U.S. Pat. No. 5,489,283, issued Van Tilburg on Feb. 6, 1996, U.S. Pat. No. 5,569,231, issued to Emenaker et al. on Oct. 29, 1996, and U.S. Pat. No. 5,620,430, issued to Bamber on Apr. 15, 1997, the disclosure of each of which is incorporated by reference herein.

V. Treating Articles With Composition

In preparing absorbent articles to carry out the methods of the present invention, the skin care composition is applied such that during wear, at least some portion of the composition will transfer from the treated article to the wearer's skin. That is, skin care composition is either applied directly to one or more wearer contacting surfaces, or is applied in alternate locations or means such that the skin care composition is readily available for transfer from one or more wearer contacting surfaces during use without intervention by the user/caregiver. (For example, materials positioned beneath the wearer contacting surface, encapsulated compositions, etc.) Of course, to effectuate delivery of composition to those body regions most susceptible to skin roughness, it will be preferred to include the composition on the portion of the topsheet and cuffs that will contact the wearer's buttocks, genitals, intertriginous and anal regions during wear. Additionally, the composition may be applied to other article regions for delivery to one or more of the wearer's hips, abdomen, back, waist, sides, thighs, etc. Suitable methods include spraying, printing (e.g., flexographic printing), coating (e.g., contact slot coating, gravure coating), extrusion, or combinations of these application techniques, e.g. spraying the skin care composition on a rotating surface, such as a calender roll, that then transfers the composition to the desired portion of the article. The skin care composition can also be applied as a solid material via any of a variety methods, for example extrusion.

When applied to the article's topsheet, the manner of applying the composition to the article should be such that the topsheet does not become saturated with the composition, at least in the region corresponding to the liquid discharge region of the article, if the composition is hydrophobic in nature. If the topsheet becomes saturated with the composition in the liquid discharge region, there is a greater potential for the composition to block the topsheet openings, reducing the ability of the topsheet to transmit liquid to the underlying absorbent core. Also, saturation of the topsheet is not required to obtain the therapeutic and/or protective benefits. Similarly, saturation of other treated article components may not be necessary or desired to transfer sufficient composition for desired skin benefits. Particularly suitable application methods will apply the composition primarily to the outer surface of the diaper topsheet.

The minimum level of composition to be applied to the article's wearer-contacting surface is an amount effective for providing the therapeutic, protective and/or skin conditioning benefits when the composition is delivered pursuant to the present methods. The level of composition applied will depend on various factors, including the article component treated, the relative amount of surface area of the wearer-contacting surface not treated with the composition, the composition's content and the like. In general, with compositions that are relatively hydrophobic and are to be applied to essentially all of the topsheet, the composition is preferably applied to the article topsheet in an amount ranging from about 0.1 mg/in$^2$ (0.016 mg/cm$^2$) to about 15 mg/in$^2$ (2.33 mg/cm$^2$), more preferably from about 1 mg/in$^2$ (0.16 mg/cm$^2$) to about 10 mg/in$^2$ (1.55 mg/cm$^2$). It will be recognized that higher levels of skin care composition may be applied to other article components where fluid handling properties are not impacted (e.g., cuffs, waist band, side panels, etc.). It will also be recognized that for compositions that are relatively hydrophilic, higher add-on levels may be used on the topsheet without adversely impacting liquid handling properties to an unacceptable degree. Conversely, higher levels of a hydrophilic composition may be undesired when applied to components (e.g., cuff, waist) other than the topsheet, to avoid wicking of exudates to the edges of the article which may result in leakage.

Because the composition is preferably substantially immobilized on the surface of the region treated, relatively small amounts of composition are needed to impart the desired skin care benefits. Applicants believe that the ability to use low levels to impart the desired skin benefits is due to the fact that pursuant to the methods described herein, composition is continuously, automatically delivered as articles are worn. As indicated, the ability to use relatively low levels of skin care composition, allows the article's topsheet to maintain its liquid transfer properties in the liquid discharge region.

The composition can be applied nonuniformly to the wearer contacting surface of the article. By "nonuniform" it is meant that the amount, location, pattern of distribution, etc. of the composition can vary over the wearer-contacting surface, and may further vary over specific regions of the article. For example, to maintain the liquid handling performance of the topsheet, it may be desired to apply the composition nonuniformly to the topsheet, particularly if the composition is hydrophobic in nature. In this regard, some portions of the treated surface of the article (and regions thereof) can have greater or lesser amounts of composition, including portions of the surface that do not have any composition on it. When the composition is relatively hydrophobic, in one such preferred embodiment the surface of the topsheet will have regions where no composition is applied, particularly in areas of the topsheet that correspond to the crotch region of the article. As used herein, the crotch region of the article is the rectangle, defined below, that is centered longitudinally and laterally about the article's crotch point. The "crotch point" is determined by placing the article on a wearer in a standing position and then placing an extensible filament around the legs in a figure eight configuration. The point in the article corresponding to the point of intersection of the filament is deemed to be the crotch point of the article. (It is understood that the crotch point is determined by placing the absorbent article on a wearer in the intended manner and determining where the crossed filament would contact the article.) With regard to incontinence devices (e.g., diapers, adult incontinent articles), the length of the crotch region corresponds to 40% of the absorbent article's total length (i.e., in the y-dimension). With regard sanitary napkins, the length of the crotch region corresponds to 80% of the absorbent article's total length. The width of the crotch region is equivalent to the width of the widest absorbent core component as measured at the crotch point. (As used herein, "absorbent core" components are those materials involved with acquiring, transporting, distributing and/or storing body liquids. As such, the term absorbent core does not include the topsheet or backsheet of the absorbent article.) By way of illustration, for an incontinent article having a length of 20 in. and a core width at the crotch point of 4 in., the crotch region is the rectangle, centered on the crotch point, having a length of 8 in. and a width of 4 in.

Surprisingly, while the topsheet or other components comprising the composition are treated nonuniformly (e.g., microscopic or macroscopic regions where no composition is applied), during wear of the article, the composition is transferred to the wearer even in regions of the skin corresponding to untreated regions within the topsheet or other components. The amount and uniformity of composition transferred to the skin is believed to depend on several factors, including, for example, application pattern of the skin care composition, contact of the wearer's skin to the treated article surface, friction created during wear time between the wearer's skin and the treated region, warmth generated from wearer to enhance the transfer of the composition, the composition's properties, the materials which constitute the composition, and the like.

Where the composition is applied nonuniformly, any pattern may be utilized, including, for example, application of small droplets (obtained via, e.g., spraying) discrete dots (obtained via, e.g., gravure printing), stripes that run in the longitudinal or lateral direction of the article (obtained via contact slot coating), spirals that run in the longitudinal or lateral direction, etc., patterned prints, etc. In those embodiments where the topsheet comprises discrete, untreated regions, the percent open area of the region of the topsheet that corresponds to the crotch region of the article can vary widely. (As referred to herein, the "percent open area" of the topsheet is determined by (i) measuring the surface area of the topsheet that overlies the crotch region, (ii) measuring the total surface area of the untreated region(s) in this portion of the topsheet and (iii) dividing the measurement in (ii) by the measurement in (i). As used herein, "untreated" means a region of the topsheet having less than about 0.01 mg/in$^2$ (0.0016 mg/cm$^2$) of the composition. In this regard, the percent open area may be from about 1% to about 99%, from about 5% to about 95%, from about 10% to about 90%, from about 15% to about 85%, from about 20% to about 80%, from about 25% to about 75%, from about 30% to about 70%, or from about 35% to about 65%. The percent open area required to achieve the desired composition effect and the desired liquid handling properties of the topsheet will be dictated largely by the characteristics of the composition (in particular the composition's contents and its relative hydrophobicity/hydrophilicy properties). One skilled in the art will appreciate that the desired percent open area will be readily determined through routine experimentation.

In general, with compositions that are relatively hydrophobic and are to be applied such that regions of the topsheet are not coated with the composition, the composition is preferably applied to the article topsheet in an amount ranging from about 0.05 mg/in$^2$ (0.0078 mg/cm$^2$) to about 35 mg/in$^2$ (5.43 mg/cm$^2$), more preferably from about 1 mg/in$^2$ (0.16 mg/cm$^2$) to about 25 mg/in$^2$ (3.88 mg/cm$^2$), still more preferably 4 mg/in$^2$ (0.62 mg/cm$^2$) to about 20 mg/in$^2$ (3.1 mg/cm$^2$). It will be recognized that for compositions that are relatively hydrophilic, higher add-on levels may be used without adversely impacting liquid handling properties of the topsheet to an unacceptable degree. Of course, for articles having relatively high percent open areas in the crotch, greater add-on levels may be obtainable without adversely affecting liquid handling by the topsheet.

In one preferred embodiment for carrying out the present methods, the topsheet of the articles utilized will comprise stripes of composition that run in the article's longitudinal direction. These longitudinal stripes (or spirals) are separated by longitudinal stripes where little or no composition is applied to the topsheet. In these embodiments, each stripe of composition will typically have a width of from about 0.1 in. to about 0.75 in., more typically from about 0.1 in. to about 0.5 in., and the width of the stripes containing no composition will typically be from about 0.1 in. to about 1 in., more typically from about 0.15 to about 0.5 in. These ranges are applicable to typical infant diaper designs. For larger products such as adult incontinent products, these ranges may be higher.

Skin care composition can also be applied in nonuniform patterns on other article components. In these cases, the open area is calculated by the rectangle defined by the perimeters of the skin care composition.

The composition can be applied to the article at any point during assembly. For example, the composition can be applied to the finished disposable absorbent product before it has been packaged. The composition can also be applied to a given component (e.g., topsheet, cuffs, sides, waiste, etc.), at the converting site or by the material supplier, before it is combined with the other raw materials to form a finished disposable absorbent product. Again, the composition can be applied to other zones of the article such that the composition will migrate to one or more wearer contacting surfaces during use.

The composition is typically applied from a melt thereof to the article. Since in a preferred embodiment, the composition melts at significantly above ambient temperatures, it is usually applied as a heated composition to the article. Typically, the composition is heated to a temperature in the range from about 35° to about 150° C., preferably from 40° to about 100° C., prior to being applied to the article. Once the melted composition has been applied to the article, it is allowed to cool and solidify. Preferably, the application process is designed to aid in the cooling/set up of the composition.

In applying compositions to the articles, contact slot coating, spraying, gravure coating, extrusion coating methods are preferred. One such method involves slot coating of the composition on the article's topsheet after the topsheet is assembled with the other raw materials into a finished product.

VI. Test Methods

A. Evaluating Skin Smoothness

1. Test Summary

Two different infant diaper products are evaluated to determine if there is a difference in the skin smoothness in the diaper area in an average infant population associated with the use of a test product (i.e. comprising a skin care composition on one or more wearer contacting surface) over that associated with the control product (an equivalent product, with the exception that it contains no skin care composition).

2. Investigational Plan

2.1 Study Design

This study is conducted at an qualified clinical research organization (CRO) and should comply with good clinical practices (GCP) guidelines. The study is a randomized, parallel, double-blind design in which the personnel conducting the measurements and the panelists will be unaware of the treatment assignment of the study participants. A sufficient number of health infants will be recruited from the general population residing in the geographical area of the clinical site to participate and complete this study such that one hundred (100) infants, fifty (50) per group, complete the study.

Two subject groups will participate in this study. Both groups will include healthy infants, each comprising approximately 50% males and 50% females. The two groups will be age and/or diaper size balanced (when wearing appropriately sized diapers). The two groups will consist of healthy infants not taking medications for conditions other than those that are routine for that age, such as common cold/flu. All infants will present no evidence of serious dermatological conditions (e.g. not atopic).

All infants who meet enrollment criteria will be assigned to use the control product for one week (baseline). At the end of one week, the infants will be randomly assigned into one of two possible groups: One group will remain on the control product for one week; the other group will use a test product for a period of one week. As such, the total duration of the test for both control and test product users is two weeks.

At the point when infants are randomized into two groups, no further use of ointments, creams, lotions, corn starch, or powders will permitted on the skin in the diaper area during the remaining period of the study. The use of soap, water, baby wipes, or cleansing gels is permitted at diaper changes and baths.

The skin smoothness (i.e., skin cast replicas and D-Squame tapes) of infants will be evaluated at the following times: at the end of the one week baseline (visit 2); and at the end of the one week treatment phase (visit 3). The parents will change the absorbent article two (2) hours before their scheduled time for the skin smoothness measurements. The infant should be bathed immediately prior to the overnight diaper the night before the visit and not again until after the visit.

2.2 Procedure

Visit 1:

Prior to coming to the first visit, parents will change the child two hours before their scheduled time of arrival at the clinical facility. Additionally, they will have been instructed to bathe the child immediately prior to the overnight diaper change the night before Visit 1 and not to bathe the child again until after completion of Visit 1. Eligible children will be weighed and assigned to the appropriate size diaper, based on weight and diaper fit criteria. Instructions for study participation and product use will be discussed with participants, and they will receive copies of the instructions, along with a copy of their consent form. The caregiver of each child enrolled in the study will receive a sufficient amount of control diapers to use during the baseline week of the study. The caregiver will be instructed that the child is to be bathed the evening before Visit 2 and not again until after Visit 2 has been completed. The caregiver of each child will be instructed to bring the child back to the clinical site one week later and to change the child 2 hours before their scheduled time of arrival to the site.

Figure 2:
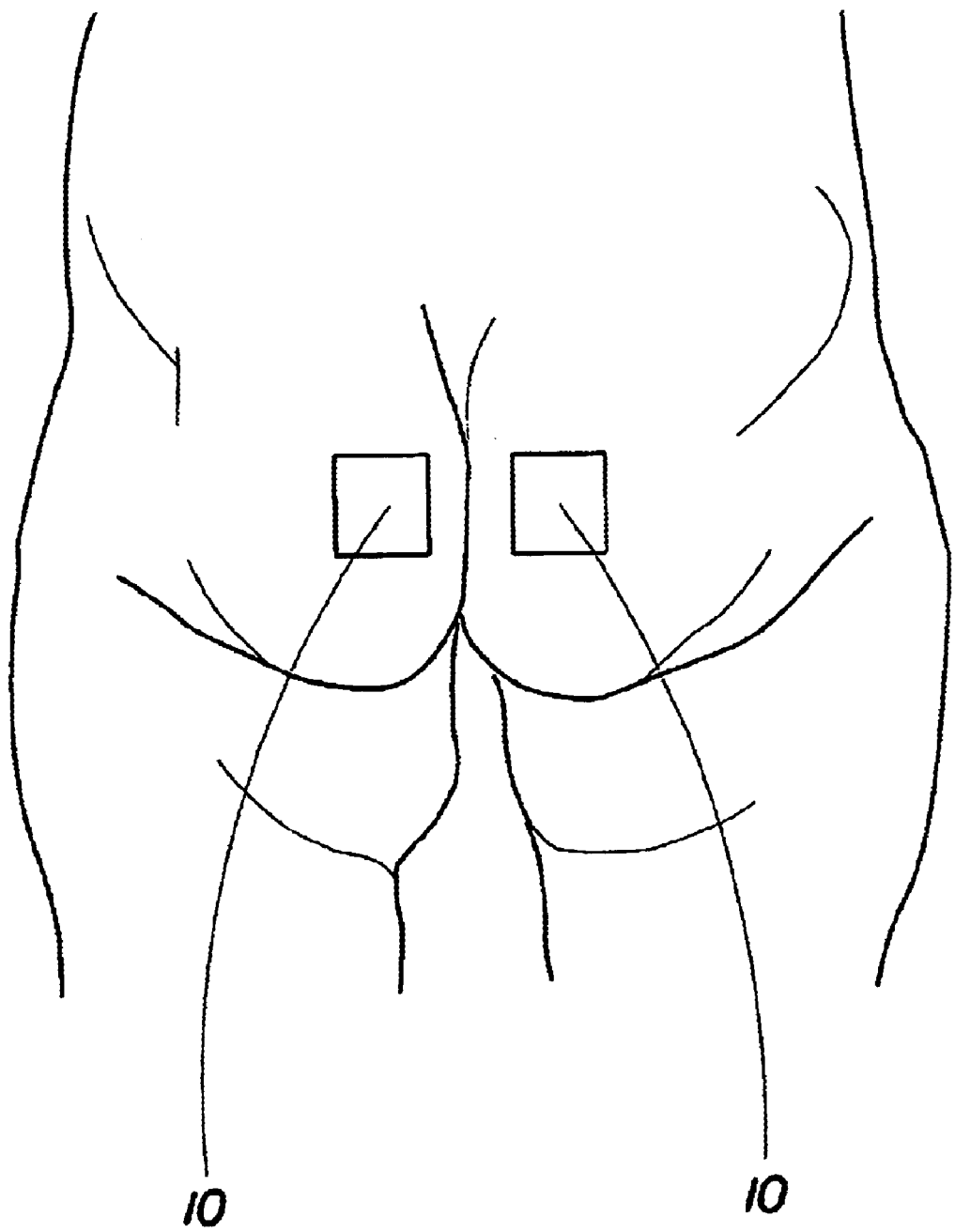
FIG. 2 depicts the regions of a wearer of an absorbent article that are assessed for skin smoothness.

Visit 2:

Upon arrival to the clinical site and prior to diaper removal, it will be confirmed that the child was changed into a clean diaper 2 hours before. Children who do not comply with the 2 hour requirement will be rescheduled as appropriate to fulfill this requirement. Children who had a bowel movement during the 2 hour interval, will be changed into one of their assigned diapers, using the normal hygiene practices of the caregiver, and re-scheduled for 2 hour later. Children who meet the 2 hour requirement will be randomly assigned to receive the control or test product. After treatment assignment, the children will acclimate for 15 minutes in a temperature (22+/−2° C.)/humidity (45%+/−5%) controlled room. Following acclimation, the child's diaper will be removed and a 1.0×1.0 inch area demarcated using indelible ink in the lower third of the left and right buttocks of the child, beginning approximately 0.5 inch from the gluteal groove. Referring to FIG. 2, demarcated areas 10 on a subjects buttocks are depicted. If the infant presents any visible signs of a skin eruption (i.e., rash, papules, etc.) at that location, the measurement area can be moved no more than 0.5 inch in any direction (except towards the gluteal groove). If a totally clear skin site cannot be found within this area, the site can be located adjacent to the site outlined on the contralateral buttocks. If evidence of skin eruption is also present at this area, the infant will be dropped from participation in the study. Skin casts and D-Squame tape samples will be obtained only from infants who meet all of the above requirements. A skin cast will be obtained from the central portion of one of the demarcated areas. A D-Squame tape sample will be obtained from the central portion of the contralateral demarcated area, shown in FIG. 2. The assignment of left/right buttocks to skin cast and D-Squame measurement will be done randomly.

Each child's caregiver will receive a supply of their assigned diaper to use over the following week. Caregivers will be instructed to use only their assigned diaper and to suspend immediately the use of any creams, ointments, lotions or any other skin care products on the diapered skin of their child, until the completion of the study one week later. The use of wipes, soap, water or any other items that are part of the cleansing routine of the caregiver at diaper changes is permissible. The caregiver will be instructed that the child is to be bathed the evening before Visit 3 and not again until after Visit 3 has been completed. The caregiver also will be instructed to bring the child back to clinical facility for Visit 3 at their scheduled time and to change the child into a clean diaper 2 hours after their scheduled Visit 3 appointment.

Visit 3:

Upon arrival to the clinical site, all of the procedures followed during Visit 2, will be repeated up to and including obtaining the skin cast and D-Squame samples from each infant. After sampling has been completed, the children will be discharged from the study.

2.3 Study Population

As indicated, one hundred (100) infants are expected to complete this study. Two subject groups will participate in this study, each group comprising approximately 50% males and 50% females. The two groups will be age and/or diaper size balanced (when wearing appropriately sized diapers). The study population will consist of healthy infants not taking medications for conditions other than those that are routine for that age, such as common cold/flu.

2.3.1 Inclusion Criteria

Each Infant must:

have no serious dermatological conditions in the diaper area, be full time disposable diaper user.

be in general good health to meet the weight requirements for the specific diapers to be evaluated in the study.

have a caregiver willing to not use lotions, creams, powders, or other skin preparations in the diaper area after completion of visit two and until the end of the study.

have a caregiver willing to have the child refrain from bathing or swimming after the last diaper change the night before the scheduled skin evaluation visits until the visit is complete.

The eligibility of each potential infant is also determined by the completion of a medical and dermatological history questionnaire. Subjects will be excluded from this study for one or more of the reasons listed below under exclusion criteria.

2.3.2 Exclusion Criteria

Infant does not meet the inclusion criteria.

Infant has been ill within the past 4 days which, in the opinion of the Clinical Research Organization's Principle Investigator, may interfere with the test.

Infant has diarrhea (soft stools) within four days before the test.

Infant is being administered medication which, in the opinion of the Clinical Research Organization's Principle Investigator, might influence the skin condition or might increase bowel movement frequency, e.g. oral antibiotics, anti-fungal agents, antihistamines, corticosteroids taken orally or topically applied on the skin.

Infant has significant eruption in the diaper area or damaged skin in or around the test site, including sunburn, active dermal lesions or scars, and/or moderate/severe skin conditions in the diaper area.

Infant exhibits significant hypersensitivity, rash or other abnormal skin reactions or lesions to topical or systemic medications, sunscreens, cosmetics, lotions, creams or fragrances within one year prior to study initiation.

Infant has diabetes or chicken pox.

Infant has psoriasis, ichthyosis.

Infant has any other medical condition that could compromise the study.

2.4 Test Materials

The two treatment groups that will be included in this study are as follows:

Test Group: will use diapers having a skin care composition that is transferred to the wearer during use.

Control Group: will use equivalent diapers to the Test Group, but the diapers have no skin care composition that is transferred to the wearer during use.

2.5 Randomization

Each subject will be randomly assigned, using a statistically valid randomization schedule, at Visit 2 to either control product or to test product. Test Group and Control Group will be balanced for sex and age or diaper size. Twins (or multiple births) will be assigned to use the same product.

2.6 Regimen & Compliance With Treatment

The infants will arrive at the investigative site at approximately the same time of the day for each visit. The infants are expected to wear their assigned products only. No ointments, creams, lotions, or powders should be used on the skin in the diaper area after Visit 2. The use of soap, water, baby wipes, or cleansing gels is permitted at diaper changes. They will be asked to bathe the child the evening before the visit, immediately prior to putting on the overnight diaper and not again until after their scheduled visit.

Subjects should come to the site such that when their skin measurements are taken, they will be wearing a product for two hours (+/−15 min.). If the participant presents with a bowel movement, the diaper will be changed and the subject asked to remain or report back after two hours for skin measurements. If the subject has a second bowel movement during the two hour wait period or cannot return, they will be disqualified from the study.

2.7 Blinding

All subjects will be blinded to the products they are using. Products will not be labeled with an identifiable label. Site personnel doing measurements will also be blinded to the products being dispensed and used.

2.8 Discontinuation of Subjects From the Study 2.8.1 Removal of Subjects failure to appear for any of the study visits.

non-compliance—if they use their own diapers during the study, or if they use lotion, powders, etc., or bathing within excluded time periods.

any illness which the Clinical Research Organization's Principle Investigator decides may effect the results of the study, especially diarrhea.

the infant being uncooperative to the point where skin measurements are not possible.

a rash-free site is not available on the defined area of the buttocks for skin cast or D-Squame measurements.

2.8.2 Replacement of Subjects

In case of subject discontinuation, no replacement subjects will be recruited due to the short duration of this study.

2.9 Observations and/or Measurements 2.9.1 Skin Cast Replicas

Skin casts will be taken at Visits 2 and 3 by a technician experienced in the casting technique.

1. Materials: All materials are available commercially for this application from CuDerm, Inc. (Dallas, Tex.). Supplies needed are:
   a. Flexico Silflo Impression material
   b. Flexico Silflo Catalyst
   c. CuDerm Replica Locating Rings (1.25 inch o.d.; 0.75 inch i.d.).

2. Principles: The procedure yields a replicate of skin surface topographic features. The resulting replica is evaluated by image analysis to obtain a numerical estimate of the smooth/rough characteristics of the section of the skin acquired in the replica.

3. Procedure: After diaper removal, the subject is placed in a prone position, face down on an appropriately padded examination table. As the subject will have to remain relatively immobile for approximately two (2) to three (3) minutes in this position, the parent/guardian should remain with the subject in order to assist technical staff in maintaining correct positioning during the replica procedure.

One site will be demarcated using indelible ink on the buttocks. The site selection process will define a 1.0×1.0 inch area in the lower third of the left or right buttocks of the child, beginning approximately 0.5 inch from the gluteal groove. (See FIGS. 2a and 2b for an illustration of where skin cast replica should be taken.) Site selection will be made by placing CuDerm Replica Locating Rings (1.25 inch o.d., 0.75 inch i.d.) symmetrically within the demarcated area. The blue orientation tab of the locating ring will be positioned such that the length of the tab is parallel to the separation line between the buttocks. It is important during placement of the adhesive ring that the skin surface is not distorted or fine topological features will be lost.

Replicas of each test site will be generated utilizing Silflo Silicone Impression Material. The appropriate amount of catalyst will be added such that replicas dry rapidly without loss of sensitivity to topographical details. When polymerization of the elastomer is complete, the replicas will be removed from the subject, allowed to complete the drying process, labeled, and stored in an appropriate storage envelope.

4. Cast Analysis

The instrumental analysis of the skin casts will be done using the Rodenstock RM600 2-D/3-D Measuring Station (Optische Werke G. Rodenstock, Munich, Germany). The procedure for measurement is described in detail in the manufacturer's instrument manual. The primary parameters to be used are summarized below.

The section of the cast to be scanned is a 1.0 cm. square area of the cast defined symmetrically around the geometric center of the cast.

Select the 3-dimensional display setting for a roughness measurement over the defined area.

Secure the cast on the traverse table and position the table in the center of the base plate of the distance sensor.

Focus the laser on the measuring surface.

Adjust the sensor distance as recommended by the manufacturer.

Follow the measurement program (contained in the instrument manual) to complete the measurement.

Repeat for all skin casts in the study, without changing any of the scanning parameters (i.e., scannable area location and dimensions, sensor distance, etc.).

The roughness value provided by the measurement software will be used as the end-point to evaluate effects of the control or test article on skin smoothness.

2.9.2 D-Squame tape samples

D-Squame® samples will be taken at the buttocks site contralateral to that used for the skin cast acquisition. The site will define a 1.0×1.0 inch area in the lower third of the left or right buttocks of the child, beginning approximately 0.5 inch from the gluteal groove. (See FIGS. 2a and 2b for an illustration of where skin cast replica should be taken.) D-Squame samples will be taken using commercially available adhesive discs (CuDerm, Dallas, Tex.). These are discs of approximately 0.5 inches in diameter which are routinely used to evaluate shedding of the outer layers of the stratum corneum. The surface of the tape coated with adhesive is applied to the infant's skin at the designated site of the buttocks, the tape is then tapped gently with a glass rod to ensure uniform adhesion to the skin and is then removed immediately and affixed to a grading board for subsequent evaluation. The adhesive properties of the tape are such that removal from skin occurs easily and without significant discomfort.

The extent of corneocyte shedding is determined from each D-Squame disc by comparing the disc to the commercially-available D-Squame comparator scale, available from CuDerm, and assigning the appropriate numerical value to the respective disc.

3. Statistics

For purposes of the present disclosure, evidence of a test product improvement is demonstrated with skin cast and/or D-Squame and is defined as a statistical or non-statistical (as defined above) difference between test and control at the end of the study or between test group Visit 3 and test group Visit 2 (i.e., within subject comparison versus baseline): (a) for the study group as a whole; or (b) for any gender or age or diaper size subset of the study group; or (c) any Visit 2 grade subset for the D-Squame test.

Evaluation of Skin Cast Replica Data

Analysis of covariance models should be used for the analysis of the Visit 3 skin cast replica data. The covariate to be used in these analyses should be the Visit 2 data. The initial analysis of covariance model should include a covariate by treatment interaction term to determine whether the Visit 3 data values are influenced by the values seen at the start of the treatment comparison period (i.e., the Visit 2 data).

If there is no significant covariate by treatment interaction, a reduced model without the interaction term should be used to determine treatment differences. Least square means (i.e., treatment means adjusted for the covariate) and their standard errors should be used for the treatment comparisons.

If the covariate by treatment interaction is significant, a separate slopes analysis of covariance model (i.e., a model with separate regression lines being estimated for each treatment group) should be used to determine treatment differences for different values of the covariate. For each treatment group, the predicted regression line with upper and lower 90% confidence limits on the mean should be plotted. To aid examination, plots of each pair of treatments should be displayed. Visual examination of the pairwise plots should indicate for which values of the covariate the treatment groups are different and for which values of the covariate the treatment groups are not different. Those covariate values for which the 90% confidence limits from both treatments do not overlap indicate covariate values at which the treatments differ.

The statistical comparison between test group Visit 3 and test group Visit 2 will be done by paired t-test or a Wilcoxin Signed Rank Test (non-normally distributed).

A transformation (e.g., log) may be done prior to analysis to improve the distributional characteristics of the data (i.e., improve the homogeneity of the treatment group variances, improve the normality of the analysis of covariance residuals). Alternately, a nonparametric analog to the analysis of covariance or paired t test may be done.

Evaluation of D-Squame Tape Data

An extension of the Mantel-Haenszel strategy should be used for the analysis of the Visit 3 D-Squame data with separate analyses for each site. This involves creating contingency tables of the Visit 3 D-Squame grades (i.e., treatment by grade) with separate tables for subjects who had the same D-Squame grade at Visit 2. Mean scores are computed for the D-Squame grades; mean score differences are combined across the separate contingency tables to compute a chi-square statistic over all subgroups. The Mantel-Haenszel statistic from each individual contingency table will be determined to establish whether treatment-related differences occur within any of the subgroups. The same methodology will be used to determine whether within subject changes from Visit 2 to Visit 3 are significant for the test group.

B. Transfer of Skin Care Composition to Wearer's Skin

Overview

This method uses a removable skin analog material that is placed on a wearer's skin for a controlled period of time. After the skin analog has been removed, it is extracted using an appropriate solvent and the amount of skin care composition deposited thereon is determined using known analytical methods. The method is described for use with treated infant diapers. One of skill in the art will recognize the appropriate changes for other skin care compositions, absorbent articles, or wearer types.

Subjects

Approximately equal numbers of male and female infants should be selected using the following inclusion and exclusion criteria. Sufficient infants should be selected to ensure that there are at least fifteen subjects per condition and transfer time who complete all aspects of the test.

Inclusion Criteria a. Healthy infant b. Caregiver willing to not use lotions, creams, powders or other skin preparations in the diaper area for the duration of the test.

c. Infants who wear disposable diapers full time d. Caregiver willing to give child bath the evening before the study and not again until after completion of the study e. Caregiver will to have child refrain from swimming from the evening before the study until after completion of the study.

f. Preferably, infants who have infrequent bowel movements

Exclusion Criteria a. The infant has been ill within the last four days b. Diarrhea (soft stool) any time during the four days before the test c. Medication which might increase frequency of bowel movements (e.g., oral antibiotics, anti fungal agents, corticosteroids)

d. Damaged skin in or around the test site (e.g., from sunburn, active dermal lesions, or the like)

e. Known allergies or irritation from adhesive or skin care ingredients

Materials

In Vivo Transfer

Skin Analog: Dermatological Tape—TEGADERM Tape No. 1622W available from 3M Health Cares, St. Paul, Minn.

Sample Container Glass jar with closure available from VWR Scientific, West Chester, Pa. as catalog Number 15900-242

Tape Release Powder Baby powder (comprising only talc and fragrance) available from Johnson & Johnson, New Brunswick, N.J.

Surgical Gloves Available from Best Manufacturing Co., Menlo Ga., as product 6005PFM.

Extraction and Analysis

Extraction Solvent Dichloromethane, available from Sigma-Aldrich of St. Louis, Mo. as 27056-3

Stearyl alcohol Aldrich 25876-8

1-Hexadecanol Aldrich 25874-1

Dispensing Flask 10 ml

Gas Chromatograph Flame ionization Detector, Hewlwtt Packard Model 5890 is suitable.

Column Capillary column: Chrompack CP Sil-5 CB, 2 meters ×0.25 mm id, 0.12 micron film thickness fused silica capillary (no substitutions)

Instrumental Data Must be able to reproducibly determine areas of peaks of

System interest.

Method

In Vivo Transfer

A. Confirm from the subject's caregiver that the subject has been bathed within the last 24 hours and that no lotions, powders, etc. have been applied to the diapered region of the subject's skin since bathing.

B. Wearing the surgical gloves, place the subject on the table and remove his/her diaper.

C. Turn the subject on his/her stomach.

D. Remove the release liner from a TEGADERM tape and lightly brush J&J Baby Powder over the adhesive surface (Wear surgical gloves, or the like, during application to prevent contamination of the tape). Provide sufficient powder such that there is a light coat of powder over all of the tape except the edges. (This step is done to keep the tape from adhering too aggressively to the child's skin.).

Figure 3A:
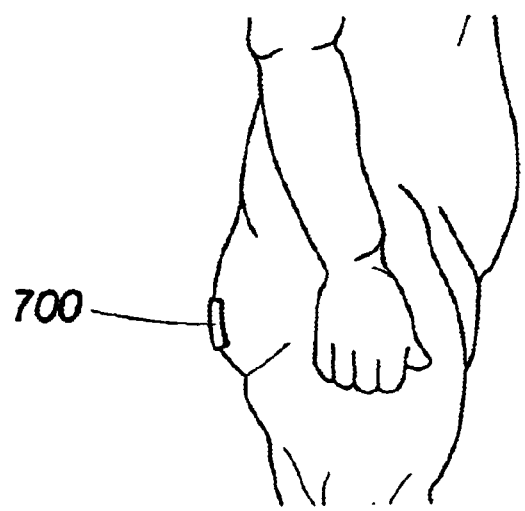
FIG. 3a is a side view showing placement of tape for assessing the amount of skin care composition transferred.
Figure 3B:
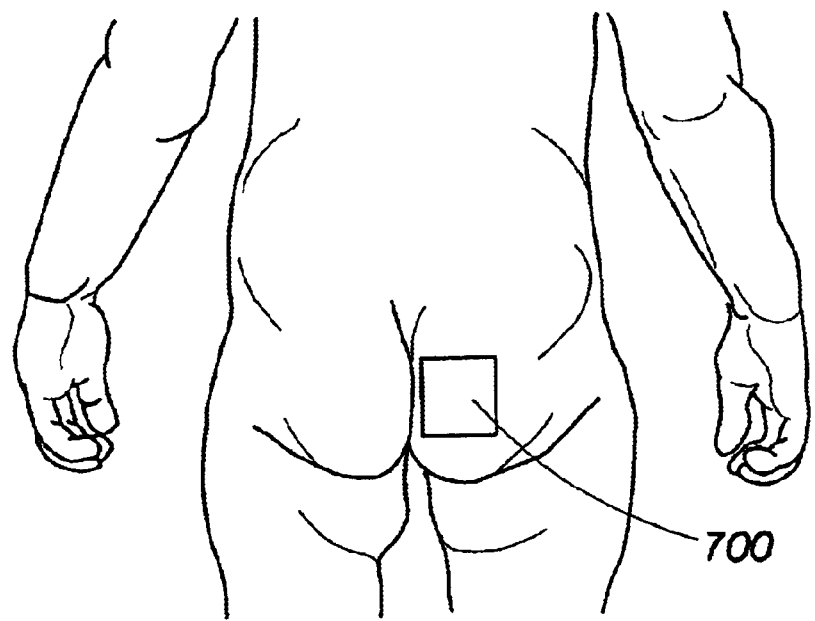
FIG. 3b is plan view showing placement of the tape for assessing level of skin care composition transfer.

E. FIGS. 3a and 3b illustrate placement location for the TEGADERM tape, shown in those figures as tape 700. Apply the tape 700 to the child's right buttock. The tape 700 is to be applied to the highest point on the child's buttock immediately adjacent to, but not in, the child's gluteal groove. A second tape 700 may be applied to measure transfer at two time increments or the effect of an additional diaper. If a second tape is used, apply the tape 700 on the left buttock using the procedure described above.

F. Change diapers according to the following protocol: 3 hour transfer time—1 diaper; 6 hour transfer time—2 diapers (change at 3 hours); 24 hour transfer times ad lib by caregiver. For 24 hour transfer times the following additional instructions are to be followed:

1. Use only water and a washcloth for cleaning the diapered area for the duration of the test. Do not use baby wipes. Avoid touching the area around the tapes with hands or any cleaning implement.

2. Do not use skin care products (lotions, ointments, creams, soap, etc.) for the duration of the test.

3. Do not bathe the subject for the duration of the test.

4. Use only the test diapers. Record the time of each diaper change.

5. Record the time of any bowel movement and clean the subject with water and a wash cloth.

G. Record the time each diaper was applied for all test diapers.

H. Recall the subject near the end of the predetermined transfer time.

I. Remove the test diaper. If the child has had a bowel movement, the study personnel should remove the tape 700 and discard it (the subject has then completed the test and data from that subject are not included in the analysis). If the subject has urinated, the tape 700 will be acceptable for analysis as described below.

J Test facility personnel should wear surgical gloves and remove the tape 700 by grasping the edge of the tape 700 with tweezers and gently peeling the remaining portion of the tape 700 from the skin.

K. Place the used tape 700 in one of the glass jars and close the lid. Make sure the jar is properly labeled for subsequent sample identification.

L. At the completion of the test collect all of the samples in the jars for analysis as described below.

Extraction and Analysis

This method is designed for use with the preferred skin care composition, the skin care composition of Table 1. One of ordinary skill in the art will recognize what adaptions may be necessary to extract and analyze the level of other skin care compositions. In principle: 1) one of the major ingredients of the composition is extracted from the skin analog using an appropriate solvent; 2) gas chromatographic or other appropriate quantitative analytical techniques are then used to determine the level of the major ingredient in the extract; 3) amount of skin care composition is calculated per unit area based on amount of major ingredient in extract and the area of the tape.

Internal Standard/Extraction Solvent

Prepare an internal standard/extraction solvent by accurately weighing 100±2 mg of 1-hexadecanol into a small beaker. Dissolve the 1-hexadecanol in dichloromethane and transfer to a 1 liter volumetric flask. Rinse the beaker 3 more times with dichloromethane transferring each rinse portion to the volumetric flask. Fill the volumetric flask to volume and mix well. This solution will be used to deliver the internal standard and extract skin care composition from the tapes. When not being used, this container should be kept tightly capped to prevent evaporation of solvent.

Calibration Standard

Prepare a calibration standard of known concentration by accurately weighing (±0.1 mg) 10±1 mg of the stearyl alcohol into a 100 ml volumetric flask. Record the weight of stearyl alcohol used. Add the internal standard/extraction solvent to the flask and mix to dissolve. Fill to volume and mix well. When not being used, this container should be kept tightly capped to prevent evaporation of solvent. This solution will be used to determine the relative response of the stearyl alcohol to the 1-hexadecanol internal standard for calibration of the instrument.

Preparation and Calibration of the Gas Chromatograph

All equipment should be installed, operated and maintained according to manufacturer's recommendations.

Install the column and check all the gas flows with the column oven at 100° C. and the injection port and detector at operating temperatures. The GC will be operated under the following conditions:

Carrier Gas: Hydrogen (Helium may be used); flow rate 1.5 ml/min

Injection Port: 325° C.; Split vent flow 30 ml/min; Septum purge 2 ml/min; straight through liner with glass wool plug; Merlin microseal.

Injection volume: 2 μl split

FID Detector: 350° C.; set gas flows according to manufacturer suggestions. Typical gas flows are 400 ml/minute for air, 30 ml/minute for hydrogen and 30 ml/minute for the auxiliary (make up) gas.

Column Oven: 100° C. ramped at 15° C./minute to 325° C.; hold for 10 minutes

Insure that all connections are tight and leak free. Ignite the detector and allow it to stabilize. Condition the column at 325° C. for 30 minutes. Clean the syringe with dichloromethane as needed. The syringe should also be rinsed with dichloromethane several times after each injection. Make several blank runs with injections of dichloromethane to ensure that a good baseline is obtained and that no extraneous peaks are present in the chromatogram. If extraneous peaks are present or baseline is not suitable, trouble shoot and correct problem(s).

Calibrate the instrument using the calibration standard prepared previously. Consult the data system manufacturer's instructions for the proper sequence of operations. Calculations should be performed in a manner similar to that described in CALCULATIONS below in order to provide the desired result.

Sample Analysis Procedure

1) Remove the lid from the sample jar and add 10 ml of the extraction solvent/internal standard solution using the dispensing flask. Replace the cap and swirl the contents to insure that the tape 700 is not adhering to the sides of the jar and is totally submersed in solvent. Repeat for all samples.

2) Allow the samples to sit 16 hours (typically done overnight).

3) Swirl the contents of the jar to mix. Using a transfer pipette, transfer an aliquot of the sample extract to a properly labeled autosampler vial. Cap the vial. Replace jar lid and retain until analyses are complete. Repeat for all samples.

4) Place the vials in the autosampler in random order and start the analyses using the GC conditions described above. The first vial should be a dichloromethane blank. Several "check" standards should be placed (about every 20th sample) through out the run to verify correct operation.

5) At the completion of the run, check each chromatogram to insure proper analysis. If a problem is suspected, trouble shoot and correct. Reanalyze samples as needed.

Calculations

The total micrograms of stearyl alcohol in each sample extract is calculated based on the relative response of the stearyl alcohol peak to that of the 1-hexadecanol internal standard. The ratio of the peak areas is multiplied by the relative response factor (determined at time of instrument calibration) and the micrograms of internal standard in the extract to yield the total μg of stearyl alcohol in a sample.

Instrument Calibration

Determine the instrumental relative response factor for the stearyl alcohol and the internal standard based on the areas of the stearyl alcohol and 1-hexadecanol peaks in the calibration standard chromatogram.

$$\text{Response factor } (R_f) = \frac{\text{Area}_{inst}}{\text{weight}_{inst}} \times \frac{\text{weight}_{sa}}{\text{Area}_{sa}} \times 10$$

where Area$_{inst}$ GC peak area for the internal standard in calibration standard Area$_{sa}$ GC peak area for the stearyl alcohol in calibration standard weight$_{inst}$ actual micrograms of the internal standard used to prepare internal standard/extraction solvent weight$_{sa}$ micrograms of the stearyl alcohol used to prepare the calibration standard Test Sample Calculations Calculate the total micrograms of stearyl alcohol in each test sample using the peak areas from the test sample chromatogram in the following equation:

$$\text{Total } \mu_g \text{ } SA = \frac{\text{Area}_{sa}}{\text{Area}_{inst}} \times R_f \times \frac{\text{weight}_{inst}}{100}$$

where Area$_{inst}$ GC peak area for the internal standard in test sample

Area$_{sa}$ GC peak area for the stearyl alcohol in test sample weight$_{inst}$ actual micrograms of the internal standard used to prepare internal standard/extraction solvent Report amount of skin care composition transferred in mg/cm² where:

$$\text{Composition Transferred} = \frac{0.001 \times \mu g \text{ of stearyl alcohol}}{(\text{concentration of stearyl alcohol in composition}) \times (\text{tape area})}$$

For the method described above the concentration of stearyl alcohol in the composition is 41% and the tape patch measures 4.4 cm×4.4 cm. Therefore Composition Transferred =(0.001×μg of stearyl alcohol)/(0.41×4.4 cm×4.4 cm) 0.000126×μg of stearyl alcohol (mg/cm²)

VII. Specific Examples

The following are specific illustrations of (a) treating diaper topsheets with skin care compositions and (b) methods of the present invention which utilize articles comprising those topsheets. Similar approaches may be utilized to treat other components for providing treated articles for use in the present methods.

EXAMPLE 1

Preparation of an Absorbent Article Having a Topsheet Comprising a Skin Care Composition A. Preparation of Skin Care Composition A skin care composition (Composition A) is made by mixing the following melted (i.e., liquid) components together: Petrolatum (available from Witco Corp., Greenwich, Conn. as White Protopet®), Stearyl Alcohol (available from The Procter & Gamble Company, Cincinnati, Ohio as CO1897) and aloe extract (available from Madis Botanicals, Inc., South Hackensack, N.J. as Veragel Lipoid in Kaydol). The weight percentages of these components are shown in Table I below:

TABLE I

| Component | Weight % |
|---|---|
| Petrolatum | 58 |
| Stearyl Alcohol | 41 |
| Aloe | 1 |

B. Preparation of a Treated Article by Contact Slot Coating

Composition A is placed into a heated tank operating at a temperature of 170° F. The composition is subsequently applied with a contact applicator (using, for example, a Meltex EP45 hot melt adhesive applicator head having 5 slots and operating at a temperature of 170° F.) onto the topsheet of an article in a striped pattern where the stripes run in the article's longitudinal direction. Specifically, 5 stripes are applied, each stripe measuring 0.25 in. wide (i.e., in the articles lateral direction) and 11.75 in. long at an add-on level=7.7 mg/in$^2$ (12 g/m$^2$, 1.19 mg/cm$^2$). The distance between the stripes is 0.31 in.

The article to which skin care composition is added in this example is commercially available Pampers Premium (Size 4) diapers, available from Procter & Gamble, Cincinnati, Ohio.

EXAMPLE 2

Method of Improving Skin Condition

An infant weighing 20 lbs. who has dry, chafed skin is diapered for a period of 10 days using the diaper of Example 1. The infant's diaper is changed according to the routine patterns of the caregiver. (Typical diapering patterns consist of changes every three to four hours during the day and application of a fresh diaper before overnight sleep.) No intervention by the caregiver, in the form of manual application of skin protective or conditioning products, occurs during this period. During the 10 day period, the subject is observed to have improved skin smoothness.

EXAMPLE 3

Method of Improving Skin Condition

An active incontinent adult weighing 165 lbs. who constantly uses absorbent articles and who persistent dry skin uses an adult incontinent product analogous to the diaper of Example 1 for a period of at least about 7 days. The subject's article is changed according to the routine patterns of the user. (Typical changing patterns consist of changes every four to five hours during the day and application of a fresh article before overnight sleep.) No intervention by the user, in the form of manual application of skin protective or conditioning products, occurs during this period. At the end of the 7 day period, the is subject is observed to have improved skin smoothness.

EXAMPLE 4

Method of Improving Skin Condition

An infant weighing 32 lbs. is diapered for a period of at least about 5 days using the diaper of Example 1 during overnight sleep only. (That is, a untreated article is used throughout the day.) The infant's diaper is changed according to the routine patterns of the caregiver. No intervention by the caregiver, in the form of manual application of skin protective or skin conditioning products, occurs during this period. At the end of the 5 day period, the subject is observed to have skin smoothness

EXAMPLE 5

Method of Improving Skin Condition

An infant weighing 25 lbs. experiences an episode of diarrhea that results in red and roughened skin. Based on experience with conventional (untreated) diapers, the caregiver expects to need to manually apply skin care products for at least 1 week to completely resolve the skin condition. Instead, Example 1 diapers are used continuously for 1 week. With no intervention by the caregiver in the form of manual application of skin care products, the skin is clear and smooth by the end of the 1 week period, with improvements noticed within about 2 days.

What is claimed is:

1. A method for improving skin condition of a wearer in the area covered by a treated absorbent article, the method comprising the following steps:
    (a) applying to the wearer an unused, treated absorbent article having a skin care composition that improves skin smoothness upon transfer to the skin of the wearer;
    (b) transferring to the wearer at least a portion of the skin care composition from the unused, treated article during wear whereby the unused, treated article is transformed to a used, treated article;
    (c) removing the used, treated article from the wearer; and
    (d) repeating steps (a), (b) and (c) with six or more additional treated article for at least a 24 hour period;
whereby at least 0.03 mg/in$^2$ (0.0047 mg/cm$^2$) is transferred to the wearer's skin over the 24 hour period so as to cause an improvement in skin condition in the area of a wearer covered by the treated absorbent articles having a skin care composition, relative to skin covered by untreated absorbent articles that do not comprise the skin care composition, is manifested in terms of a skin condition measure selected from the group consisting of: (1) smoother skin as measured via image analysis of skin casts and (2) reduced squamous cell release in the D-Squame tape analysis.

2. The method of claim 1 wherein untreated absorbent articles which do not comprise a skin care composition are applied to the wearer intermittently.

3. The method of claim 1 wherein treated absorbent articles comprising a skin care composition are applied to the wearer only during overnight sleep.

4. The method of claim 1 wherein steps (a) and (b) are repeated at six times per day for at least 4 days.

5. The method of claim 1 wherein the skin in the area of a wearer covered by treated absorbent articles having a skin care composition is at least about 10% smoother than skin covered by untreated absorbent articles that do not comprise the skin care composition, as measured by one or both of image analysis of skin casts and by D-Squame tape analysis.

6. The method of claim 5 wherein the skin covered by treated absorbent articles is at least about 15% smoother than skin covered by untreated absorbent articles that do not comprise the skin care composition, as measured by one or both of image analysis of skin casts and D-Squame tape analysis.

7. The method of claim 1 wherein in step (b), at least about 0.01 mg/in$^2$ (0.0016 mg/cm$^2$) of the skin care composition is transferred to the wearer during use of the treated article over a 3 hour wear period.

8. The method of claim 7 wherein in stop (b), at least about 0.05 mg/in$^2$ (0.0078 mg/cm$^2$) of the skin care composition is transferred to the wearer's skin during use of the treated article over a 3 hour wear period.

9. The method of claim 1 wherein in step (b), at least about 0.1 mg/in$^2$ (0.016 mg/cm2) of the skin care composition is transferred to the wearer's skin during use of the treated article over a 24 hour wear period.

10. The method of claim 9 wherein in step (b), from about 0.03 mg/in$^2$ (0.0047 mg/cm$^2$) to about 18 mg/in$^2$ (2.79 mg/cm$^2$) of the skin care composition is transferred to the wearer's skin during use of the treated article.

11. The method of claim 1 wherein the skin care composition transferred to the wearer comprises a member selected from the group consisting of petroleum-based emollients; fatty acid ester type emollients; alkyl ethoxylate type emollients; fatty acid ester ethoxylates emollients; fatty alcohol type emollients; polysiloxane-type emollients; sucrose ester fatty acids; polyethylene glycol and derivatives thereof; sorbitol and derivatives thereof, trihydroxysterin and derivatives thereof, propylene glycol and derivatives thereof; glycerine and derivatives thereof; triethylene glycol and derivatives thereof; spermaceti or other waxes; fatty acids; fatty alcohol ethers; propoxylated fatty alcohols; fatty esters of polyhydroxy alcohols; lanolin and its derivatives; kaolin and its derivatives; alantoin; aluminum hydroxide gel; calamine; cocoa butter, cod liver oil; kaolin; lanolin; mineral oil; shark liver oil; white petrolatum; talc; topical starch; zinc acetate; zinc carbonate; zinc oxide; live yeast cell derivatives; aldioxa; aluminum acetate; microporous cellulose; cholecalciferol; colloidal oatmeal; cysteine hydrochloride; dexpanthanol; Peruvian balsam oil; protein hydrolysates; racemethionine; sodium bicarbonate; Vitamin A; and mixtures thereof.

12. The method of claim 11 wherein the skin care composition comprises a petroleum-based emollient selected from the group consisting of mineral oil, petrolatum, and mixtures thereof.

13. The method of claim 12 wherein the skin care composition comprises petrolatum.

14. The method of claim 1, wherein the article of step (a) comprises:
A) a liquid impervious backsheet;
B) a liquid pervious topsheet having a body facing surface and a garment facing surface, wherein at least a portion of the topsheet comprises the skin care composition and wherein the skin care composition is semi-solid or solid at 20° C.; and
C) an absorbent core positioned between the topsheet and the backsheet.

15. The method of claim 14 wherein the skin care composition comprises a member selected from the group consisting of petroleum-based emollients; fatty acid ester type emollients; alkyl ethoxylate type emollients; fatty acid ester ethoxylates emollients; fatty alcohol type emollients; polysiloxane-type emollients; sucrose ester fatty acids; polyethylene glycol and derivatives thereof; sorbitol and derivatives thereof, trihydroxysterin and derivatives thereof; propylene glycol and derivatives thereof; glycerine and derivatives thereof; triethylene glycol and derivatives thereof; spermaceti or other waxes; fatty acids; fatty alcohol ethers; propoxylated fatty alcohols; fatty esters of polyhydroxy alcohols; lanolin and its derivatives; kaolin and its derivatives; alantoin; aluminum hydroxide gel; calamine; cocoa butter; cod liver oil; kaolin; lanolin; mineral oil; shark liver oil; white petrolatum; talc; topical starch; zinc acetate; zinc carbonate; zinc oxide; live yeast cell derivatives; aldioxa; aluminum acetate; microporous cellulose; cholecalciferol; colloidal oatmeal; cysteine hydrochloride; dexpanthanol; Peruvian balsam oil; protein hydrolysates; racemethionine; sodium bicarbonate; Vitamin A; and mixtures thereof.

16. The method of claim 14 wherein the skin care composition comprises a petroleum-based emollient selected from the group consisting of mineral oil, petrolatum, and mixtures thereof.

17. The method of claim 16 wherein the skin care composition comprises petrolatum.

18. The method of claim 14 wherein the skin care composition is applied to the liquid pervious topsheet such that one or more regions of the topsheet are not treated with skin care composition.

19. The method of claim 18 wherein the skin care composition is applied to the topsheet in the form of a plurality of stripes that are separated by a plurality of stripes having no skin care composition.

20. A method for improving skin condition of a wearer in the area covered by a treated absorbent article, the method comprising the following steps:
(a) applying to the wearer an unused treated absorbent article having a skin care composition that improves skin condition upon transfer to the skin of the wearer;
(b) transferring to the wearer at least a portion of the skin care composition from the unused treated article during wear whereby the unused treated article is transformed to a used treated article;
(c) removing the used, treated article from the wearer; and
(d) repeating steps (a), (b), and (c) with six or more additional unused, treated articles for at least a 24 hour period;
wherein the skin care composition is semi-solid or solid at 20° C. and comprises:
(i) from about 5 to about 95% of an emollient; and
(ii) from about 5 to about 95% of one or more agents capable of immobilizing the emollient on or in the treated article, the one or more immobilizing agents having a melting point of at least about 35° C.
whereby at least 0.03 mg/in$^2$ (0.0047 mg/cm$^2$) is transferred to the wearer's skin over the 24 hour period so as to cause an improvement in skin condition in the area of a wearer covered by the treated absorbent articles having a skin care composition, relative to skin covered by untreated absorbent articles that do not comprise the skin care composition, is manifested in terms of a skin condition measure selected from the group consisting of: (1) smoother skin as measured via image analysis of skin casts and (2) reduced squamous cell release in the D-Squame tape analysis.

21. The method of claim 20 wherein untreated absorbent articles which do not comprise a skin care composition are applied to the wearer intermittently.

22. The method of claim 20 wherein treated absorbent articles comprising a skin care composition are applied to the wearer only during overnight sleep.

23. The method of claim 20 wherein steps (a) and (b) are repeated at least six times per day for at least 4 days.

24. The method of claim 20 wherein the skin care composition comprises a petroleum-based emollient selected from the group consisting of mineral oil, petrolatum, and mixtures thereof.

25. The method of claim 24 wherein the skin care composition comprises petrolatum.

26. The method of claim 20 wherein the improvement in skin smoothness in the a of aria wearer covered by absorbent articles having a skin care composition, relative to skin covered by untreated absorbent articles that do not comprise the skin care composition, is manifested in terms of one or both of: (1) smoother skin as measured via image analysis of skin casts; and (2) reduced squamous cell release in the D-Squame tape analysis.

27. The method of claim 26 wherein the skin in the area of a wearer covered by treated absorbent articles having a skin care composition is at least about 10% smoother, as measured by one or both of image analysis of skin casts and by D-Squame tape analysis.

28. The method of claim 27 wherein the skin is at least about 15% smoother, as measured by image analysis of skin casts and/or by D-Squame tape analysis.

29. The method of claim 20 wherein in step (b), at least about 0.01 mg/in$^2$ (0.0016 mg/cm$^2$) of the skin care composition is transferred to the wearer during use of the treated article treated with the skin care composition.

30. The method of claim 29 wherein in step (b), at least about 0.05 mg/in$^2$ (0.0078 mg/cm$^2$) of the skin care composition is transferred to the wearer's skin during use of the treated article treated with the skin care composition.

31. The method of claim 30 wherein in step (b), at least about 0.1 mg/in$^2$ (0.016 mg/cm$^2$) of the skin care composition is transferred to the wearer's skin during use of the treated article treated with the skin care composition.

32. The method of claim 31 wherein in step (b), from about 0.01 mg/in$^2$ (0.0016 mg/cm$^2$) to about 5 mg/in$^2$ (0.78 mg/cm$^2$) of the skin care composition is transferred to the wearer during use of the treated article treated with the skin care composition.

33. The method of claim 20 wherein the skin care composition transferred to the wearer comprises a member selected from the group consisting of petroleum-based emollients; fatty acid ester type emollients; alkyl ethoxylate type emollients; fatty acid ester ethoxylates emollients; fatty alcohol type emollients; polysiloxane-type emollients; sucrose ester fatty acids; polyethylene glycol and derivatives thereof; sorbitol and derivatives thereof, trihydroxysterin and derivatives thereof; propylene glycol and derivatives thereof; glycerine and derivatives thereof; triethylene glycol and derivatives thereof; spermaceti or other waxes; fatty acids; fatty alcohol ethers; propoxylated fatty alcohols; fatty esters of polyhydroxy alcohols; lanolin and its derivatives; kaolin and its derivatives; alantoin; aluminum hydroxide gel; calamine; cocoa butter; cod liver oil; kaolin; lanolin; mineral oil; shark liver oil; white petrolatum; talc; topical starch; zinc acetate; zinc carbonate; zinc oxide; live yeast cell derivatives; aldioxa; aluminum acetate; microporous cellulose; cholecalciferol; colloidal oatmeal; cysteine hydrochloride; dexpanthanol; Peruvian balsam oil; protein hydrolysates; racemethionine; sodium bicarbonate; Vitamin A; and mixtures thereof.

34. The method of claim 33 wherein the skin care composition comprises a petroleum-based emollient selected from the group consisting of mineral oil, petrolatum, and mixtures thereof.

35. The method of claim 34 wherein the skin care composition comprises petrolatum.

36. The method of claim 20 wherein the skin care composition is applied to a liquid pervious topsheet of the treated absorbent article such that one or more regions of the topsheet are not treated with skin care composition.

37. The method of claim 36 wherein the skin care composition is applied to the topsheet of the treated absorbent article in the form of a plurality of stripes that are separated by a plurality of stripes having no skin care composition.

* * * * *

UNITED STATES PATENT AND TRADEMARK OFFICE
CERTIFICATE OF CORRECTION

PATENT NO.    : 6,710,223 B1
DATED         : March 23, 2004
INVENTOR(S)   : Van Rijswijck et al.

It is certified that error appears in the above-identified patent and that said Letters Patent is hereby corrected as shown below:

Column 3,
Line 29, please delete "aricle" and insert therefor -- article --.

Column 14,
Line 10, please delete "$(CHOH)_2(CHOR^3)(CHOH)—CH2OH$" and insert therefor -- $(CHOH)_2(CHOR^3)(CHOH)—CH_2OH$ --.

Column 21,
Line 42, between "in" and "U.S." please insert -- co-pending --.

Column 24,
Line 39, please delete "wom" and insert therefore -- worn --.

Column 33,
Line 43, please delete "comeocyte" and insert therefore -- corneocyte --.

Column 35,
Line 53, between "Data" and "Must" please insert -- System --.
Line 54, after "of" please insert -- interest. --.
Line 55, please delete "System interest."

Column 40,
Line 5, after the second occurrence of "the" please delete "is".
Line 47, please delete "article" and insert therefore -- articles --.
Line 65, between "at" and "six" please insert -- least --.

Column 41,
Line 15, please delete "stop" and insert therefore -- step --.
Line 35, after "thereof" please delete "," (the comma) and insert therefor -- ; -- (a semi-colon).
Line 41, after "butter" please delete "," (the comma) and insert therefor -- ; -- (a semi-colon).

UNITED STATES PATENT AND TRADEMARK OFFICE
CERTIFICATE OF CORRECTION

PATENT NO.   : 6,710,223 B1
DATED        : March 23, 2004
INVENTOR(S)  : Van Rijswijck et al.

It is certified that error appears in the above-identified patent and that said Letters Patent is hereby corrected as shown below:

Column 43,
Line 13, please delete "a of aria" and insert therefor -- area of a --.

Signed and Sealed this

Twenty-sixth Day of July, 2005

JON W. DUDAS
*Director of the United States Patent and Trademark Office*